US009732145B2

(12) United States Patent
Ordentlich et al.

(10) Patent No.: US 9,732,145 B2
(45) Date of Patent: Aug. 15, 2017

(54) **ANTIBODIES DIRECTED TO *BACILLUS ANTHRACIS* PROTECTIVE ANTIGEN**

(71) Applicants: Arie Ordentlich, Ramat Gan (IL); Einat Ben Arie, Ness Ziona (IL); Ronit Rosenfeld, Ness Ziona (IL); Hadar Marcus, Petah-Tiqwa (IL); Batel Lachmi, Tel-Aviv (IL)

(72) Inventors: Arie Ordentlich, Ramat Gan (IL); Einat Ben Arie, Ness Ziona (IL); Ronit Rosenfeld, Ness Ziona (IL); Hadar Marcus, Petah-Tiqwa (IL); Batel Lachmi, Tel-Aviv (IL)

(73) Assignee: THE ISRAEL INSTITUTE OF BIOLOGICAL RESEARCH (IIBR), Ness-Ziona (IL)

( * ) Notice: Subject to any disclaimer, the term of this patent is extended or adjusted under 35 U.S.C. 154(b) by 0 days.

(21) Appl. No.: 14/813,690

(22) Filed: Jul. 30, 2015

(65) Prior Publication Data

US 2016/0145324 A1    May 26, 2016

Related U.S. Application Data

(60) Provisional application No. 62/031,295, filed on Jul. 31, 2014.

(51) Int. Cl.
*A61K 39/00* (2006.01)
*A61K 39/40* (2006.01)
*A61K 39/395* (2006.01)
*C07K 16/12* (2006.01)
*A61K 45/06* (2006.01)

(52) U.S. Cl.
CPC .......... *C07K 16/1278* (2013.01); *A61K 45/06* (2013.01); *A61K 2039/505* (2013.01); *C07K 2317/24* (2013.01); *C07K 2317/622* (2013.01); *C07K 2317/76* (2013.01)

(58) Field of Classification Search
CPC .......... C07K 16/12; A61K 39/40; A61K 45/06
See application file for complete search history.

(56) References Cited

U.S. PATENT DOCUMENTS 7,456,264 B2   11/2008   Keler et al.
7,601,351 B1   10/2009   Rosen et al.

FOREIGN PATENT DOCUMENTS

GB          2480298 A     11/2011
WO     WO 2013126746   *  8/2013  ............ C07K 16/28

OTHER PUBLICATIONS

Plotkins, S. and Grabenstein, J. D., "Countering Anthrax: Vaccines and Immunoglobulins", Clinical Infectious Diseases, pp. 129-136, vol. 46 (Jan. 2008).

(Continued)

*Primary Examiner* — Ja'Na Hines
(74) *Attorney, Agent, or Firm* — Browdy and Neimark, PLLC

(57) ABSTRACT

This disclosure generally relates to therapeutic antibodies for treating *Bacillus anthracis* (*B. anthracis*) infection, to specific variants thereof, pharmaceutical composition comprising them and to methods for their use.

12 Claims, 5 Drawing Sheets

(56) References Cited

OTHER PUBLICATIONS

Turnbull, P.C., et al., "MICs of Selected Antibiotics for Bacillus anthracis, Bacillus cereus, Bacillus thuringiensis, and Bacillus mycoides from a Range of Clinical and Environmental Sources as Determined by the Etest",Journal of Clinical Microbiology, pp. 3626-3634, vol. 42, No. 8 (Aug. 2004).

Rosenfeld, R., et al., "Isolation and Chimerization of a Highly Neutralizing Antibody Conferring Passive Protection against Lethal Bacillus anthracis Infection", PLoS One, vol. 4, No. 7, pp. 1-9 (Apr. 2009).

Mechaly, A., et al. ,"A Novel Mechanism for Antibody-based Anthrax Toxin Neutralization" The Journal of Biological Chemistry, pp. 32665-32673, vol. 287 No. 39 (Sep. 2012).

Mazor, O., et al., "The Challenge of Highly Pathogenic Microorganisms", Springer Science+Business Media B.V, pp. 1-317, (2010).

http://www.cdc.gov/anthrax/index.html Anthrax, Centers for Diease Control and Prevention, (Sep. 2015).

Cohen, S. et al., "Attenuated Nontoxinogenic and Nonencapsulated Recombinant Bacillus anthracis Spore Vaccines Protect against Anthrax", Infection and Immunity, pp. 4549-4558, vol. 68, No. 8, (Aug. 2000).

Reuveny, S. et al., "Search for Correlates of Protective Immunity Conferred by Anthrax Vaccine", Infection and Immunity, pp. 2888-2893, vol. 69, No. 5, (May 2001).

Köhler, G. and Milstein, C.,"Continuous cultures of fused cells secreting antibody of predefined specificity" Nature, pp. 495-497, vol. 256, Aug. 1975).

Mosmann, T., "Rapid Colorimetric Assay for Cellular Growth and Survival: Application to Proliferation and Cytotoxicity Assays", Journal of Immunological Methods, pp. 55-63, vol. 65 (Jun. 1983).

Benhar, I. and Reiter, Y., "Phage Display of Single-Chain Antibody Constructs", Current Protocols in Immunology, pp. 1-31, (May 2002).

\* cited by examiner

PA29VH w.t.

CAGGTTCAACTGCAGCAGTCTGGGGCTGAGCTGGTGAAGCCTGGGGCCTCAGTGAAGATGTCCTGCAAGGCTTCTGGCTACACATATTACCaATTACAATATGCACTGGGTACAGCA
GACACCTGGACAGGGCCTGGAATGGATTGGCGCTATTTATCCACGAAACTGGTGATACTTCCTACGAAGTCAGAAGTTCAAAGGCAAGGCCACATTGACTGCAGACAAATCCTCCAGCA
CAGCCTACATGCAGCTCAGCAGCCTGACATCTGAGGATTCTGCGGTCTATTACTGTGCAAGAGACGGGTTTGCTTACTGGGGCCAAGGGACCACTCTCACAGTC

QVQLQQSGAELVKPGASVKMSCKASGYIFTNYNMHWVQQTPGQGLEWIGAIYPRTGDTSYNQKFKGKATLTADKSSSTAYMQLSSLTSEDSAVYYCARDGFAYWGQGTTLTV

PA29VL w.t.

GATATCCAGATGACACAGACTACATCTCCCTGTCTGCCTCTCTGGGAGACAGAGTCACCATCAGTTGCAGGGCAAGTCAGGACATTAGCAATTATTTAAACTGGTATCAGCAGAA
ACCAGATGGAACTGTTAAACTCCGATCTACTACACATCAAGATTACACTCAGAAGTTCAGTGGCAGTGGGTCTGGAACAGATTATTCTCTCACCATTAGCAACCT
GGAGGAAGAAGATATTGCCACTTACTTTTGCCAACAGGGTAAAACGCTTCCGTGGACGTTCGGTGGAGGCACCAAGCTGGAAATCAAA

DIQMTQTTSSLSASLGDRVTISCRASQDISNYLNWYQQKPDGTVKLLIYYTSRLHSEVPSRFSGSGSGTDYSLTISMLEEEDIATYFCQQGKTLPWTFGGGTKLEIK

PA29mut29VH

CAGGTTCAACTGCAGCAGTCTGGGGCTGAGCTGGTGAAGCCTGGGGCCTCAGTGAAGATGTCCTGCAAGGCTTCTGGCTACACATATTACCAATTACAATATGCACTGGGTACAGCA
GACACCTGGACAGGGCCTGGAATGGATTGGCGCCATTTATCCACGAAACTGGTGATACTTCCTACAATCAGAAGTTCAAAGGCAAGGCCACATTGACCGCAGACAAATCCTCCAGCA
CAGCCTACATGCAGCTCAGCAGCCTGACATCTGAGGATTCTGCGGTCTATTACTGTGCAAGAGACGGGTTTGCTTACTGGGGCCAAGGGACCACTCTCACAGTC

QVQLQQSGAELVKPGASVKMSCKASGYIFTNYNMHWVQQTPGQGLEWIGAIYPRTGDTSYNQKFKGKATLTADKSSSTAYMQLSSLTSEDSAVYYCARDGFAYWGQGTTLTV

PA29mut29VL

GATATCCAGATGACACAGACTACATCTCCCTGTCTGCCTCTCTGGGAGACAGAGTCACCATCAGTTGCAGGGCAAGTCAGGACATTAGCAATTATTTAAACTGGTATCAGCAGAA
ACCAGATGGAACTGTTAAACTCCGATCTACTACACATCAAGGAGTCCGTCAGTGGCAGTGGGTCTGGAACAGATTATTCTCTCACCATTAGCAACCT
GGAGGAAGAAGATATTGCCACTTACTACTGCCAACAGGGTAAAACGCTTCGGTGGAGGCACCAAGCTGGAAATCAAA

DIQMTQTTSSLSASLGDRVTISCRASQDISNYLNWYQQKPDGTVKLLIYYTSRLHSGVPSRFSGSGSGTDYSLTISNLEEEDIATYCQQGKTLPWTFGGGTKLEIK

Figure 1

PA29mut33VH

GAGGTTCAACTGCAGCAGTCTGGGGCTGAGCTGGTGAAGCCTGGGGCCTCAGTGAAGATGTCCTGCAAGGCTTCTGGCTACACATTTACCAATTACAATATGCACTGGGTACAGCA
GACACCTGGACAGGGCCTGGAATGGATTGGCGCTATTTATCCACGAACTGGTGATACTTCCTACAATCAGAAGTTCAAGGCCAAGGCCACATTGACTGCAGACAAATCCTCCAGCA
CAGCCTACATGCAGCTCAGCAGCCTGACATCTGAGGATTCTGCGGTCTATTACTGTGCAAGAGACGGGTTTGCTTACTGGGGCCAAGGGACCACTCTCACAGTC

EVQLQQSGAELVKPGASVKMSCKASGYIFTNYNMHWVQQTPGQGLEWIGAIYPRTGDTSYNQKFKGKAFLTADKSSSTAYMQLSSLTSEDSAVYYCARDGFAYWGQGTTLTV

PA29mut33VL

GATATCCGGATGACACAGACTACATCCCTGTCTGCCTCTCTGGGAGACAGAGTCACCATCAGTTGCAGGGCAAGTCAGGACATTAGCAATTATTTAAACTGGTATCAGCAGAA
GCCAGATGGAACTGTTAAACTCCTGATCTACTACACATCCAGATTACACTCAGAAGTCAGAAGTTCAGTGGCAGTGGGTCTGGAACAGATTATTCTCTCACCATTAGCAACCT
GGAGGAAGAAGATATTGCCACTTACTTTTGCCAACAGGGTAAAACGCTTCCGTGGACGTTCGGTGGAGGCACCAAGC:GgAAATCAAA

DIRMTQTTSSLSASLGDRVTISCRASQDISNYLNWYQQKPDGTVKLLIYYTSRLHSEVPSRFSGSGSGTDYSLTISNLEEEDIATYFCQQGKTLPWTFGGGTKLEIK

PA29mut39VH

CAGGTTCAACTGCAGCAGTCTGGGGCTGAGCTAGTGAAGCCTGGGGCCTCAGTGAAGATGTCCTGCAAGGCTTCTGGCTACACATTTACCAATTACAATATGCACTGGGTACAGCA
GACACCTGGACAGGGCCTGGAATGGATTGGCGCTATTTATCCACGAACTGGTGATACTTCCTACAATCAGAAGTTCAAAGGCCAAGGCCACATTGACTGCAGACAAATCCTCCAGCA
CAGCCTACATGCAGCTCAGCAGCCTGACATCTGCGGTCTATTACTGTGCAAGAGACGGGTTTGCTTACTGGGGCCAAGGGACCACTCTCACAGTC

QVQLQQSGAELVKPGASVKMSCKASGYIFTNYNMHWVQQTPGQGLEWIGAIYPRTGDTSYNQKFKGKATLTADKSSSTAYMQLSSLTSEDSAVYYCARDGFAYWGQGTTLTV

PA29mut39VL

GATATCCAGATGACACAGACTACATCCCTGTCTGCCTCTCTGGGAGACAGAGTCACCGTCAGTTGCAGGGCAAGTCAGGACATTAGCAATTATTTAAACTGGTATCAGCAGAA
ACCAGATGGAACTGTTAAACTCCTGATCTACTACACATCAAGATTACACTCAGAAGTCAGAAGTTCAGTGGCAGTGGGTCTGGAACAGATTATTCTCTCACCATTAGCAACCT
GGAGGAAGAAGATATTGCCACTTACTTTTGCCAACAGGGTAAAACGCTTCCGTGGACGTTCGGTGGAGGCACCAAGCTGGAAATCAAA

DIQMTQTTSSLSASLGDRVTVSCRASQDISNYLNWYQQKPDGTVKLLIYYTSRLHSEVPSRFSGSGSGTDYSLTISNLEEEDIATYFCQQGKTLPWTFGGGTKLEIK

Figure 2

PA29mut40VH

CAGGTCAACTGCAGCAGTCTGGGGCTGAGCTGGTGAAGCCTGGGGCTTCAGTGAAGATGTCCTGCAAGGCTTCTGGCTACACATATTTACCAATTACACAATATGCACTGGGTACAGCA
GACACCTGGACAGGGCCTGGAATGGATTGGCGCTATTTATCCACGAACTGGTGATACTTCCTACACATCAGAATGGTCAAAGGCAAGGCCACATTGACTGCAGACAAATCCTCCAGCA
CAGCCTACATGCAGCTCAGCAGCCTGACATCTGAGGATTCTGCGGTCTATTACTGTGCAAGAGACGGGTTTGCTTACTGGGGCCAAGGGACCACTCTCACAGTC

QVQLQQSGAELVKPGASVKMSCKASGYIFTNYNMHWVQQTPGQGLEWIGAIYPRTGDTSYNQKFKGKATLTADKSSSTAYMQLSSLTSEDSAVYYCARDGFAYWGQGTTLTV

PA29mut40VL

GATATCCAGATGACACAGACTACACCCTCCCTGTCTGCCTCTCTGGGAGACAGAGTCACCATCAGTTGCAGGGCAAGTCAGGACATTAGCAATTATTAAACTGGTATCAGCAGAAA
ACCAGATGGAAGCTGTAAACTCCTGATCTACTACACATCGAGAGTATACACTCAGAAGTCCCATCGAGGTTCAGTGGCAGTGGGTCTGGAACAGAGATTATTCTCACCATTAGCAACCT
GGAGGAAGAAGATATTGCCACTTACTTTGCCAACAGGGTAAAACGCTTCGGTGGAGGCACCAAGCTGGAAATCAAA

DIQMTQTTPSLSASLGDRVTISCRASQDISNYLNWYQQKPDGTVKLLIYYTSRLHSEVPSRFSGSGSGTDYSLTISNLEEEDIATYFCQQGKTLPWTFGGGTKLEIK

PA29mut41VH

CAGGTCAACTGCAGCAGTCTGGGGCTGAGCTGGTGAAGCCTGGGGTCTCAGTGAAGATGTCCTGCAAGGCTTCTGGCTACACATATTTACCAATTACACAATATGCACTGGGTACAGCA
GACACCTGGACAGGGCCTGGAATGGATTGGCGCTATTTATCCACGAACTGGTGATACTTCCTACACATCAGAATGGTCAAAGGCCAAGGCCACATTGACTGCAGACAAATCCTCCAGCA
CAGCCTACATGCAGCTCAGCAGCCTGACATCTGAGGATTCTGCGGTCTATTACTGTGCAAGAGACGGGTTTGCTTACTGGGGCCAAGGGACCACTCTCACAGTC

QVQLQQSGAELVKPGVSVKMSCKASGYIFTNYNMHWVQQTPGQGLEWIGAIYPRTGDTSYNQKFKGKATLTADKSSSTAYMQLSSLTSEDSAVYYCARDGFAYWGQGTTLTV

PA29mut41VL

GATATCCAGATGACACAGACTACATCCTCCCTGTCTGCCTCTCTGGGAGACAGAGTCACCATCAGTTGCAGGGCAAGTCAGGACATTAGCAATTATTAAACTGGTATCAGCAGAAA
ACCAGATGGAAGCTGTAAACTCCTGATCTACTACACATCAAGATTACACTCAGAAGTCCCATCAAGTTCAGTGGCAGTGGGTCTGGAACAGATTATTCTCACCATTAGCAACCT
GGAGGAAGAAGATATTGCCACTTACTTTGCCAACAGGGTAAAACGCTTCCGTGGAGGCACCAAGCTGGAAATCAAA

DIQMTQTTSSLSASLGDRVTISCRASQDISNYLNWYQQKPDGTVKLLIYYTSRLHSEVPSRFSGSGSGTDYSLTISNLEEEDIATYFCQQGKTLPWTFGGGTKLEIK

Figure 3 w.t. QVQLQQSGAELVKPGASVKMSCKASGYTFTNYNMHWVQQT

29  QVQLQQSGAELVKPGASVKMSCKASGYTFTNYNMHWVQQT

33  EVQLQQSGAELVKPGASVKMSCKASGYTFTNYNMHWVQQT

39  QVQLQQSGAELVKPGASVKMSCKASGYTFTNYNMHWVQQT

40  QVQLQQSGAELVKPGASVKMSCKASGYTFTNYNMHWVQQT

41  QVQLQQSGAELVKPGVSVKMSCKASGYTFTNYNMHWVQQT

Figure 4A w.t. PGQGLEWIGAIYPRTGDTSYNQKFKGKATLTADKSSSTAY

29  PGQGLEWIGAIYPRTGDTSYNQKFKGKATLTADKSSSTAY

33  PGQGLEWIGAIYPRTGDTSYNQKFKGKATLTADKSSSTAY

39  PGQGLEWIGAIYPRTGDTSYNQKFKGKATLTADKSSSTAY

40  PGQGLEWIGAIYPRTGDTSYNQKFKGKATLTADKSSSTAY

41  PGQGLEWIGAIYPRTGDTSYNQKFKGKATLTADKSSSTAY

Figure 4B w.t. MQLSSLTSEDSAVYYCARDGFAYWGQGTTLTV

29  MQLSSLTSEDSAVYYCARDGFAYWGQGTTLTV

33  MQLSSLTSEDSAVYYCARDGFAYWGQGTTLTV

39  MQLSSLTSEDSAVYYCARDGFAYWGQGTTLTV

40  MQLSSLTSEDSAVYYCARDGFAYWGQGTTLTV

41  MQLSSLTSEDSAVYYCARDGFAYWGQGTTLTV

Figure 4C

| | |
|---|---|
| w.t. | DIQMTQTTSSLSASLGDRVTISCRASQDISNYLNWYQQKP |
| 29 | DIQMTQTTSSLSASLGDRVTISCRASQDISNYLNWYQQKP |
| 33 | DIRMTQTTSSLSASLGDRVTISCRASQDISNYLNWYQQKP |
| 39 | DIQMTQTTSSLSASLGDRV TVSCRASQDISNYLNWYQQKP |
| 40 | DIQMTQTTPSLSASLGDRVTISCRASQDISNYLNWYQQKP |
| 41 | DIQMTQTTSSLSASLGDRVTISCRASQDISNYLNWYQQKP |

Figure 5A

| | |
|---|---|
| w.t. | DGTVKLLIYYTSRLHSEVPSRFSGSGSGTDYSLTISNLEE |
| 29 | DGTVKLLIYYTSRLHSGVPSRFSGSGSGTDYSLTISNLEE |
| 33 | DGTVKLLIYYTSRLHSEVPSRFSGSGSGTDYSLTISNLEE |
| 39 | DGTVKLLIYYTSRLHSEVPSRFSGSGSGTDYSLTISNLEE |
| 40 | DGTVKLLIYYTSRLHSEVPSRFSGSGSGTDYSLTISNLEE |
| 41 | DGTVKLLIYYTSRLHSEVPSRFSGSGSGTDYSLTISNLEE |

Figure 5B

| | |
|---|---|
| w.t. | EDIATYFCQQGKTLPWTFGGGTKLEIK |
| 29 | EDIATYYCQQGKTLPWTFGGGTKLEIK |
| 33 | EDIATYFCQQGKTLPWTFGGGTKLEIK |
| 39 | EDIATYFCQQGKTLPWTFGGGTKLEIK |
| 40 | EDIATYFCQQGKTLPWTFGGGTKLEIK |
| 41 | EDIATYFCQQGKTLPWTFGGGTKLEIK |

Figure 5C

```
                          SEQUENCE LISTING

<160> NUMBER OF SEQ ID NOS: 30

<210> SEQ ID NO 1
<211> LENGTH: 321
<212> TYPE: DNA
<213> ORGANISM: Mus musculus

<400> SEQUENCE: 1
caggttcaac tgcagcagtc tggggctgag ctggtgaagc ctggggcctc agtgaagatg      60
tcctgcaagg cttctggcta catatttacc cattacaata tgcactgggt acagcagaca     120
cctggacagg gcctggaatg gattggcgct atttatccac gaactggtga tacttcctac     180
aatcagaagt tcaaaggcaa ggccacattg actgcagaca atcctccag cacagcctac      240 atgcagctca gcagcctgac atctgaggat tctgcggtct attactgtgc aagagacggg     300
tttgcttact ggggccaagg g                                               321

<210> SEQ ID NO 2
<211> LENGTH: 107
<212> TYPE: PRT
<213> ORGANISM: Mus musculus

<400> SEQUENCE: 2

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
                20                  25                  30

Asn Met His Trp Val Gln Gln Thr Pro Gly Gln Gly Leu Glu Trp Ile
            35                  40                  45

Gly Ala Ile Tyr Pro Arg Thr Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Phe Ala Tyr Trp Gly Gln Gly
            100                 105

<210> SEQ ID NO 3
<211> LENGTH: 8
<212> TYPE: PRT
<213> ORGANISM: Mus musculus

<400> SEQUENCE: 3

Ile Phe Thr Asn Tyr Asn Met His
1               5

<210> SEQ ID NO 4
<211> LENGTH: 17
<212> TYPE: PRT
<213> ORGANISM: Mus musculus

<400> SEQUENCE: 4

Ala Ile Tyr Pro Arg Thr Gly Asp Thr Ser Tyr Asn Gln Lys Phe Lys
```

```
1               5                   10                  15
Gly

<210> SEQ ID NO 5
<211> LENGTH: 7
<212> TYPE: PRT
<213> ORGANISM: Mus musculus

<400> SEQUENCE: 5

Ala Arg Asp Gly Phe Ala Tyr
1               5

<210> SEQ ID NO 6
<211> LENGTH: 303
<212> TYPE: DNA
<213> ORGANISM: Mus musculus

<400> SEQUENCE: 6
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcaga agtcccatca     180
aggttcagtg gcagtgggtc tggaacagat tattctctca ccattagcaa cctggaggaa     240
gaagatattg ccacttactt ttgccaacag ggtaaaacgc ttccgtggac gttcggtgga     300
ggc                                                                   303

<210> SEQ ID NO 7
<211> LENGTH: 101
<212> TYPE: PRT
<213> ORGANISM: Mus musculus

<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Glu Val Pro Ser Arg Phe Ser Gly
        50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Lys Thr Leu Pro Trp
                85                  90                  95

Thr Phe Gly Gly Gly
            100

<210> SEQ ID NO 8
<211> LENGTH: 11
<212> TYPE: PRT
<213> ORGANISM: Mus musculus

<400> SEQUENCE: 8

Arg Ala Ser Gln Asp Ile Ser Asn Tyr Leu Asn
1               5                   10

<210> SEQ ID NO 9
<211> LENGTH: 7
<212> TYPE: PRT
```

<213> ORGANISM: Mus musculus

<400> SEQUENCE: 9

Tyr Thr Ser Arg Leu His Ser
1               5

<210> SEQ ID NO 10
<211> LENGTH: 9
<212> TYPE: PRT
<213> ORGANISM: Mus musculus

<400> SEQUENCE: 10

Gln Gln Gly Lys Thr Leu Pro Trp Thr
1               5

<210> SEQ ID NO 11
<211> LENGTH: 336
<212> TYPE: DNA
<213> ORGANISM: Artificial Sequence
<220> FEATURE:
<223> OTHER INFORMATION: Nucleic acid sequence of the heavy chain
      variable domain of PA29mut29
<220> FEATURE:
<221> NAME/KEY: misc_feature
<223> OTHER INFORMATION: Synthetic

<400> SEQUENCE: 11
caggttcaac tgcagcagtc tggggctgag ctggtgaagc ctggggcctc agtgaagatg      60
tcctgcaagg cttctggcta catatttacc aattacaata tgcactgggt acagcagaca    120
cctggacagg gcctggaatg gattggcgcc atttatccac gaactggtga tacttcctac    180
aatcagaagt tcaaaggcaa ggccacattg accgcagaca atcctccag cacagcctac      240 atgcagctca gcagcctgac atctgaggat tctgcggtct attactgtgc aagagacggg    300
tttgcttact ggggccaagg gaccactctc acagtc                              336

<210> SEQ ID NO 12
<211> LENGTH: 112
<212> TYPE: PRT
<213> ORGANISM: Artificial Sequence
<220> FEATURE:
<223> OTHER INFORMATION: Amino acid sequence of the heavy chain variable
      domain of PA29mut29
<220> FEATURE:
<221> NAME/KEY: misc_feature
<223> OTHER INFORMATION: Synthetic

<400> SEQUENCE: 12

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
                20                  25                  30

Asn Met His Trp Val Gln Gln Thr Pro Gly Gln Gly Leu Glu Trp Ile
            35                  40                  45

Gly Ala Ile Tyr Pro Arg Thr Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Phe Ala Tyr Trp Gly Gln Gly Thr Thr Leu Thr Val
            100                 105                 110

<210> SEQ ID NO 13
<211> LENGTH: 321
<212> TYPE: DNA
<213> ORGANISM: Artificial Sequence
<220> FEATURE:
<223> OTHER INFORMATION: Nucleic acid sequence of the light chain
      variable domain of PA29mut29
<220> FEATURE:
<221> NAME/KEY: misc_feature
<223> OTHER INFORMATION: Synthetic

<400> SEQUENCE: 13

```
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat acactcagg  agtcccatca     180 aggttcagtg gcagtgggtc tggaacagat tattctctca ccattagcaa cctggaggaa     240
gaagatattg ccacttacta ttgccaacag ggtaaaacgc ttccgtggac gttcggtgga     300
ggcaccaagc tggaaatcaa a                                               321
```

<210> SEQ ID NO 14
<211> LENGTH: 107
<212> TYPE: PRT
<213> ORGANISM: Artificial Sequence
<220> FEATURE:
<223> OTHER INFORMATION: Amino acid sequence of the light chain variable
      domain of PA29mut29
<220> FEATURE:
<221> NAME/KEY: misc_feature
<223> OTHER INFORMATION: Synthetic

<400> SEQUENCE: 14

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Glu
65                  70                  75                  80

Glu Asp Ile Ala Thr Tyr Tyr Cys Gln Gln Gly Lys Thr Leu Pro Trp
                85                  90                  95

Thr Phe Gly Gly Gly Thr Lys Leu Glu Ile Lys
            100                 105
```

<210> SEQ ID NO 15
<211> LENGTH: 336
<212> TYPE: DNA
<213> ORGANISM: Artificial Sequence
<220> FEATURE:
<223> OTHER INFORMATION: Nucleic acid sequence of the heavy chain
      variable domain of PA29mut33
<220> FEATURE:
<221> NAME/KEY: misc_feature
<223> OTHER INFORMATION: Synthetic

<400> SEQUENCE: 15

```
gaggttcaac tgcagcagtc tggggctgag ctggtgaagc ctggggcctc agtgaagatg      60
tcctgcaagg cttctggcta catatttacc aattacaata tgcactgggt acagcagaca     120
```

```
cctggacagg gcctggaatg gattggcgct atttatccac gaactggtga tacttcctac    180
aatcagaagt tcaaaggcaa ggccacattg actgcagaca atcctccag cacagcctac     240 atgcagctca gcagcctgac atctgaggat tctgcggtct attactgtgc aagagacggg    300
tttgcttact ggggccaagg gaccactctc acagtc                              336
```

<210> SEQ ID NO 16
<211> LENGTH: 112
<212> TYPE: PRT
<213> ORGANISM: Artificial Sequence
<220> FEATURE:
<223> OTHER INFORMATION: Amino acid sequence of the heavy chain variable
      domain of PA29mut33
<220> FEATURE:
<221> NAME/KEY: misc_feature
<223> OTHER INFORMATION: Synthetic

<400> SEQUENCE: 16

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Met His Trp Val Gln Gln Thr Pro Gly Gln Gly Leu Glu Trp Ile
        35                  40                  45

Gly Ala Ile Tyr Pro Arg Thr Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Phe Ala Tyr Trp Gly Gln Gly Thr Thr Leu Thr Val
            100                 105                 110
```

<210> SEQ ID NO 17
<211> LENGTH: 321
<212> TYPE: DNA
<213> ORGANISM: Artificial Sequence
<220> FEATURE:
<223> OTHER INFORMATION: Nucleic acid sequence of the light chain
      variable domain of PA29mut33
<220> FEATURE:
<221> NAME/KEY: misc_feature
<223> OTHER INFORMATION: Synthetic

<400> SEQUENCE: 17

```
gatatccgga tgacacagac tacatcctcc ctgtctgcct ctctgggaga cagagtcacc    60
atcagttgca gggcaagtca ggacattagc aattatttaa actggtatca gcagaagcca   120
gatggaactg ttaaactcct gatctactac acatcaagat acactcaga agtcccatca    180 aggttcagtg gcagtgggtc tggaacagat tattctctca ccattagcaa cctggaggaa   240
gaagatattg ccacttactt ttgccaacag ggtaaaacgc ttccgtggac gttcggtgga   300
ggcaccaagc tggaaatcaa a                                              321
```

<210> SEQ ID NO 18
<211> LENGTH: 107
<212> TYPE: PRT
<213> ORGANISM: Artificial Sequence
<220> FEATURE:
<223> OTHER INFORMATION: Amino acid sequence of the light chain variable
      domain of PA29mut33
<220> FEATURE:
<221> NAME/KEY: misc_feature
<223> OTHER INFORMATION: Synthetic

<400> SEQUENCE: 18

Asp Ile Arg Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Glu Val Pro Ser Arg Phe Ser Gly
    50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Lys Thr Leu Pro Trp
                85                  90                  95

Thr Phe Gly Gly Gly Thr Lys Leu Glu Ile Lys
            100                 105

<210> SEQ ID NO 19
<211> LENGTH: 336
<212> TYPE: DNA
<213> ORGANISM: Artificial Sequence
<220> FEATURE:
<223> OTHER INFORMATION: Nucleic acid sequence of the heavy chain
      variable domain of PA29mut39
<220> FEATURE:
<221> NAME/KEY: misc_feature
<223> OTHER INFORMATION: Synthetic

<400> SEQUENCE: 19
caggttcaac tgcagcagtc tggggctgag ctagtgaagc ctggggcctc agtgaagatg      60
tcctgcaagg cttctggcta catatttacc aattacaata tgcactgggt acagcagaca     120
cctggacagg gcctggaatg gattggcgct atttatccac gaactggtga tacttcctac     180
aatcagaagt tcaaaggcaa ggccacattg actgcagaca atcctccag cacagcctac      240 atgcagctca gcagcctgac atctgaggat tctgcggtct attactgtgc aagagacggg     300
tttgcttact ggggccaagg gaccactctc acagtc                               336

<210> SEQ ID NO 20
<211> LENGTH: 112
<212> TYPE: PRT
<213> ORGANISM: Artificial Sequence
<220> FEATURE:
<223> OTHER INFORMATION: Amino acid sequence of the heavy chain variable
      domain of PA29mut39
<220> FEATURE:
<221> NAME/KEY: misc_feature
<223> OTHER INFORMATION: Synthetic

<400> SEQUENCE: 20

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Met His Trp Val Gln Gln Thr Pro Gly Gln Gly Leu Glu Trp Ile
        35                  40                  45

Gly Ala Ile Tyr Pro Arg Thr Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

```
Met Gln Leu Ser Ser Leu Thr Ser Glu Asp Ser Ala Val Tyr Tyr Cys
            85                  90                  95

Ala Arg Asp Gly Phe Ala Tyr Trp Gly Gln Gly Thr Thr Leu Thr Val
            100                 105                 110
```

<210> SEQ ID NO 21
<211> LENGTH: 321
<212> TYPE: DNA
<213> ORGANISM: Artificial Sequence
<220> FEATURE:
<223> OTHER INFORMATION: Nucleic acid sequence of the light chain
      variable domain of PA29mut39
<220> FEATURE:
<221> NAME/KEY: misc_feature
<223> OTHER INFORMATION: Synthetic

<400> SEQUENCE: 21

```
gatatccaga tgacacagac tacatcctcc ctgtctgcct ctctgggaga cagagtcacc    60
gtcagttgca gggcaagtca ggacattagc aattatttaa actggtatca gcagaaacca   120
gatggaactg ttaaactcct gatctactac acatcaagat tacactcaga agtcccatca   180
aggttcagtg gcagtgggtc tggaacagat tattctctca ccattagcaa cctggaggaa   240
gaagatattg ccacttactt ttgccaacag ggtaaaacgc ttccgtggac gttcggtgga   300
ggcaccaagc tggaaatcaa a                                             321
```

<210> SEQ ID NO 22
<211> LENGTH: 107
<212> TYPE: PRT
<213> ORGANISM: Artificial Sequence
<220> FEATURE:
<223> OTHER INFORMATION: Amino acid sequence of the light chain variable
      domain of PA29mut39
<220> FEATURE:
<221> NAME/KEY: misc_feature
<223> OTHER INFORMATION: Synthetic

<400> SEQUENCE: 22

```
Asp Ile Gln Met Thr Gln Thr Thr Ser Ser Leu Ser Ala Ser Leu Gly
1               5                   10                  15

Asp Arg Val Thr Val Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Glu Val Pro Ser Arg Phe Ser Gly
    50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Lys Thr Leu Pro Trp
            85                  90                  95

Thr Phe Gly Gly Gly Thr Lys Leu Glu Ile Lys
            100                 105
```

<210> SEQ ID NO 23
<211> LENGTH: 336
<212> TYPE: DNA
<213> ORGANISM: Artificial Sequence
<220> FEATURE:
<223> OTHER INFORMATION: Nucleic acid sequence of the heavy chain
      variable domain of PA29mut40
<220> FEATURE:
<221> NAME/KEY: misc_feature
<223> OTHER INFORMATION: Synthetic

<400> SEQUENCE: 23

```
caggttcaac tgcagcagtc tggggctgag ctggtgaagc ctggggcctc agtgaagatg      60
tcctgcaagg cttctggcta catatttacc aattacaata tgcactgggt acagcagaca    120
cctggacagg gcctggaatg gattggcgct atttatccac gaactggtga tacttcctac    180
aatcagaagt tcaaaggcaa ggccacattg actgcagaca atcctccag cacagcctac     240 atgcagctca gcagcctgac atctgaggat tctgcggtct attactgtgc aagagacggg    300
tttgcttact ggggccaagg gaccactctc acagtc                              336
```

<210> SEQ ID NO 24
<211> LENGTH: 112
<212> TYPE: PRT
<213> ORGANISM: Artificial Sequence
<220> FEATURE:
<223> OTHER INFORMATION: Amino acid sequence of the heavy chain variable
      domain of PA29mut40
<220> FEATURE:
<221> NAME/KEY: misc_feature
<223> OTHER INFORMATION: Synthetic

<400> SEQUENCE: 24

```
Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
                20                  25                  30

Asn Met His Trp Val Gln Gln Thr Pro Gly Gln Gly Leu Glu Trp Ile
            35                  40                  45

Gly Ala Ile Tyr Pro Arg Thr Gly Asp Thr Ser Tyr Asn Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Phe Ala Tyr Trp Gly Gln Gly Thr Thr Leu Thr Val
            100                 105                 110
```

<210> SEQ ID NO 25
<211> LENGTH: 321
<212> TYPE: DNA
<213> ORGANISM: Artificial Sequence
<220> FEATURE:
<223> OTHER INFORMATION: Nucleic acid sequence of the light chain
      variable domain of PA29mut40
<220> FEATURE:
<221> NAME/KEY: misc_feature
<223> OTHER INFORMATION: Synthetic

<400> SEQUENCE: 25

```
gatatccaga tgacacagac tacaccctcc ctgtctgcct ctctggggga cagagtcacc      60
atcagttgca gggcaagtca ggacattagc aattatttaa actggtatca gcagaaacca    120
gatggaactg ttaaactcct gatctactac acatcgagat tacactcaga agtcccatcg    180
aggttcagtg gcagtgggtc tggaacagat tattctctca ccattagcaa cctgaggaa     240 gaagatattg ccacttactt tgccaacag gtaaaacgc ttccgtggac gttcggtgga      300
ggcaccaagc tggaaatcaa a                                              321
```

<210> SEQ ID NO 26
<211> LENGTH: 107

```
<212> TYPE: PRT
<213> ORGANISM: Artificial Sequence
<220> FEATURE:
<223> OTHER INFORMATION: Amino acid sequence of the light chain variable
      domain of PA29mut40
<220> FEATURE:
<221> NAME/KEY: misc_feature
<223> OTHER INFORMATION: Synthetic

<400> SEQUENCE: 26

Asp Ile Gln Met Thr Gln Thr Thr Pro Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Glu Val Pro Ser Arg Phe Ser Gly
    50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Lys Thr Leu Pro Trp
                85                  90                  95

Thr Phe Gly Gly Gly Thr Lys Leu Glu Ile Lys
            100                 105

<210> SEQ ID NO 27
<211> LENGTH: 336
<212> TYPE: DNA
<213> ORGANISM: Artificial Sequence
<220> FEATURE:
<223> OTHER INFORMATION: Nucleic acid sequence of the heavy chain
      variable domain of PA29mut41
<220> FEATURE:
<221> NAME/KEY: misc_feature
<223> OTHER INFORMATION: Synthetic

<400> SEQUENCE: 27
caggttcaac tgcagcagtc tggggctgag ctggtgaagc ctggggtctc agtgaagatg      60
tcctgcaagg cttctggcta catatttacc aattacaata tgcactgggt acagcagaca     120
cctggacagg gcctggaatg gattggcgct atttatccac gaactggtga tacttcctac     180
aatcagaagt tcaaaggcaa ggccacattg actgcagaca atcctccag cacagcctac      240 atgcagctca gcagcctgac atctgaggat tctgcggtct attactgtgc aagagacggg     300
tttgcttact ggggccaagg gaccactctc acagtc                                336

<210> SEQ ID NO 28
<211> LENGTH: 112
<212> TYPE: PRT
<213> ORGANISM: Artificial Sequence
<220> FEATURE:
<223> OTHER INFORMATION: Amino acid sequence of the heavy chain variable
      domain (VH) of PA29mut41
<220> FEATURE:
<221> NAME/KEY: misc_feature
<223> OTHER INFORMATION: Synthetic

<400> SEQUENCE: 28

Gln Val Gln Leu Gln Gln Ser Gly Ala Glu Leu Val Lys Pro Gly Val
1               5                   10                  15

Ser Val Lys Met Ser Cys Lys Ala Ser Gly Tyr Ile Phe Thr Asn Tyr
            20                  25                  30

Asn Met His Trp Val Gln Gln Thr Pro Gly Gln Gly Leu Glu Trp Ile
```

```
                35                  40                  45
Gly Ala Ile Tyr Pro Arg Thr Gly Asp Thr Ser Tyr Asn Gln Lys Phe
         50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Gly Phe Ala Tyr Trp Gly Gln Gly Thr Thr Leu Thr Val
             100                 105                 110

<210> SEQ ID NO 29
<211> LENGTH: 321
<212> TYPE: DNA
<213> ORGANISM: Artificial Sequence
<220> FEATURE:
<223> OTHER INFORMATION: Nucleic acid sequence of the light chain
      variable domain of PA29mut41
<220> FEATURE:
<221> NAME/KEY: misc_feature
<223> OTHER INFORMATION: Synthetic

<400> SEQUENCE: 29
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat acactcaga gtcccatca       180 aggttcagtg gcagtgggtc tggaacagat tattctctca ccattagcaa cctggaggaa     240
gaagatattg ccacttactt ttgccaacag ggtaaaacgc ttccgtggac gttcggtgga     300
ggcaccaagc tggaaatcaa a                                               321

<210> SEQ ID NO 30
<211> LENGTH: 107
<212> TYPE: PRT
<213> ORGANISM: Artificial Sequence
<220> FEATURE:
<223> OTHER INFORMATION: Amino acid sequence of the light chain variable
      domain (VL) of PA29mut41
<220> FEATURE:
<221> NAME/KEY: misc_feature
<223> OTHER INFORMATION: Synthetic

<400> SEQUENCE: 30

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Glu Val Pro Ser Arg Phe Ser Gly
     50                  55                  60

Ser Gly Ser Gly Thr Asp Tyr Ser Leu Thr Ile Ser Asn Leu Glu Glu
 65                  70                  75                  80

Glu Asp Ile Ala Thr Tyr Phe Cys Gln Gln Gly Lys Thr Leu Pro Trp
                 85                  90                  95

Thr Phe Gly Gly Gly Thr Lys Leu Glu Ile Lys
             100                 105
```

ANTIBODIES DIRECTED TO *BACILLUS ANTHRACIS* PROTECTIVE ANTIGEN

TECHNOLOGICAL FIELD

This invention generally relates to therapeutic antibodies for treating *Bacillus anthracis* (*B. anthracis*) infection.

PRIOR ART

References considered to be relevant as background to the presently disclosed subject matter are listed below:
[1] Plotkins, S. and Grabenstein, J. D. (2008) Clin. Infect. Dis. 46: 129-136.
[2] Turnbull, P. C., et al. (2004) J Clin. Microbiol. 42: 3626-3634.
[3] http://www.cdc.gov/anthrax/index.html
[4] U.S. Pat. No. 7,456,264.
[5] GB 2480298.
[6] U.S. Pat. No. 7,601,351.
[7] Rosenfeld, R., et al. (2009) PLoS ONE 4 (7): e6351.
[8] Mechaly, A., et al. (2012) JBC 287(39): 32665-32673.
[9] Mazor, O., et al. (2010), in Shafferman, A. et al. (eds), *The Challenge of Highly Pathogenic Microorganisms*, Springer Science+Business Media B.V.
[10] Cohen, S. et al. (2000) Infect. Immun 68(8): 4549-4558.
[11] Reuveny, S. et al. (2001) Infect. Immun 69: 2888-2893.
[12] Köhler, G. and Milstein, C. (1975) Nature 256: 495-497.
[13] Mosmann, T. (1983) J Immunol. Methods 65: 55-63.
[14] Benhar, I. and Reiter, Y. (2002) Curr. Protoc. Immunol. Chapter 10: Unit 10 19B.

Acknowledgement of the above references herein is not to be inferred as meaning that these are in any way relevant to the patentability of the presently disclosed subject matter.

BACKGROUND

Anthrax is an acute disease caused by the bacterium *Bacillus anthracis* (*B. anthracis*). Most forms of the disease are lethal, and it affects both humans and animals. *B. anthracis* exerts its toxicity via the dissemination of a tripartite exotoxin comprised of protective antigen (PA), lethal factor (LF) and edema factor (EF). PA plays a critical role in anthrax pathogenesis, where it can associate with either LF to form lethal toxin (LeTx) or with EF to form the edema toxin (EdTx).

Antibiotic therapy is effective for the treatment of anthrax when administered soon after infection and before the onset of symptoms. Yet, due to the possible long-term survival of anthrax spores in the lungs, a prolonged antibiotic treatment period was recommended (1). However, antibiotic treatment/prophylaxis can be problematic in situations where their use is contraindicated, or in cases involving antibiotic resistant *B. anthracis* strains (2). Furthermore, in cases where disease has progressed and a substantial amount of anthrax toxins have been delivered to the bloodstream, antibiotic treatment is of less value, highlighting the need for additional post-exposure treatment (2).

Currently, the updated recommendations of the Centers of Disease Control and Prevention (CDC) following potential exposure to aerosolized *B. anthracis* spores include a prolonged antibiotic treatment period (at least 60 days) combined with active immunization against PA (3).

Several antibodies directed against PA were isolated and described to date, for example in the U.S. Pat. No. 7,456,264 (4), GB 2480298 (5) and U.S. Pat. No. 7,601,351 (6). Rosenfeld R. et al. (7), Mechaly A. et al. (8), and Mazor O. et al. (9), the content of each of which is incorporated herein by reference, describe the isolation and activity of the monoclonal antibody mAb 29 and its corresponding human IgG1-based chimeric antibody (cAb29), although the antibody reported in these publications was not made available to the public and there was no description of the sequence of any part of such antibody. The mAb 29 and cAb29 antibodies reported in these publications are the same antibodies which have been sequenced, described, and claimed herein. Only the present specification describes these specific antibodies in sufficient detail to place them into the hands of the public.

GENERAL DESCRIPTION

By one of its aspects the present invention provides an isolated monoclonal antibody or any antigen-binding fragment thereof which binds to *Bacillus anthracis* protective antigen, wherein the antibody comprises a heavy chain variable region comprising:
  a) the complementarity determining region CDRH1 comprising the amino acid sequence of IFTNYNMH denoted by SEQ ID NO. 3 or a variant thereof;
  b) the complementarity determining region CDRH2 comprising the amino acid sequence AIYPRTGDTSYN-QKFKG denoted by SEQ ID NO. 4 or a variant thereof; and
  c) the complementarity determining region CDRH3 comprising the amino acid sequence ARDGFAY denoted by SEQ ID NO. 5 or a variant thereof; and
a light chain variable region comprising:
  d) the complementarity determining region CDRL1 comprising the amino acid sequence RASQDISNYLN denoted by SEQ ID NO. 8 or a variant thereof;
  e) the complementarity determining region CDRL2 comprising the amino acid sequence YTSRLHS denoted by SEQ ID NO. 9 or a variant thereof; and
  f) the complementarity determining region CDRL3 comprising the amino acid sequence QQGKTLPWT denoted by SEQ ID NO. 10 or a variant thereof.

In some embodiments the heavy chain variable region is encoded by a nucleic acid sequence which is at least 70% identical to SEQ ID NO. 1 and the light chain variable region is encoded by a nucleic acid sequence which is at least 70% identical to SEQ ID NO. 6.

In other embodiments the heavy chain variable region is of the amino acid sequence denoted by SEQ ID NO. 2 or a variant thereof.

In further embodiments the heavy chain variable region comprises a substitution in at least one position selected from the group consisting of position 1 and position 16 of SEQ ID NO. 2.

In still further embodiments the heavy chain variable region comprises the amino acid residue Glu at position 1 of SEQ ID NO. 2 and is of the amino acid sequence denoted by SEQ ID NO. 16.

In some embodiments the heavy chain variable region comprises the amino acid residue Val at position 16 of SEQ ID NO. 2 and is of the amino acid sequence denoted by SEQ ID NO. 28.

In other embodiments the light chain variable region is of the amino acid sequence denoted by SEQ ID NO. 7 or a variant thereof.

In further embodiments the light chain variable region comprises a substitution in at least one position selected from the group consisting of 3, 9, 21, 57 and 87 of SEQ ID NO. 7.

In still further embodiments the light chain variable region comprises the amino acid residue Arg at position 3 of SEQ ID NO. 7 and is of the amino acid sequence denoted by SEQ ID NO. 18.

In some embodiments the light chain variable region comprises the amino acid residue Pro at position 9 of SEQ ID NO. 7 and is of the amino acid sequence denoted by SEQ ID NO. 26.

In other embodiments the light chain variable region comprises the amino acid residue Val at position 21 of SEQ ID NO. 7 and is of the amino acid sequence denoted by SEQ ID NO. 22.

In further embodiments the light chain variable region comprises the amino acid residue Gly at position 57 and the amino acid residue Tyr at position 87 of SEQ ID NO. 7 and is of the amino acid sequence denoted by SEQ ID NO. 14.

In still further embodiments the heavy chain variable region is of the amino acid sequence denoted by SEQ ID NO. 2 and the light chain variable region is of the amino acid sequence denoted by SEQ ID NO. 7.

In some embodiments the isolated monoclonal antibody is a chimeric, a humanized or a human antibody.

In other embodiments the isolated monoclonal antibody is an antibody fragment selected from the group consisting of Fv, single chain Fv (scFv), heavy chain variable region, light chain variable region, Fab, F(ab)$_2$' and any combination thereof.

In further embodiments the isolated monoclonal antibody is a neutralizing antibody.

By another one of its aspects the present invention provides an isolated chimeric antibody, or any antigen-binding fragment thereof which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof.

By yet another one of its aspects the present invention provides an isolated chimeric murine-human antibody, or any antigen-binding fragment thereof which binds to *Bacillus anthracis* protective antigen, wherein the antibody comprises a heavy chain variable region of the amino acid sequence denoted by SEQ ID NO. 2 and a light chain variable region of the amino acid sequence denoted by SEQ ID NO. 7.

The present invention further provides a bispecific molecule comprising the antibody as herein defined.

By still another one of its aspects the present invention provides an isolated nucleic acid molecule comprising a nucleotide sequence encoding an antibody according to the invention or any antigen-binding fragment thereof.

The present invention further provides an expression vector comprising the isolated nucleic acid molecule according to the invention.

By another one of its aspect the present invention provides a host cell transfected with the isolated nucleic acid molecule or with the expression vector.

The present invention further provides an immunoconjugate comprising the antibody according to the invention or any antigen-binding fragment thereof and an additional anti-anthrax agent.

In some embodiments the additional anti-anthrax agent as herein defined is selected from the group consisting of a cytotoxic agent, an antibiotic, a radioactive label and an additional antibody.

By yet another one of its aspects, the present invention provides a pharmaceutical composition comprising as an active ingredient the isolated monoclonal antibody or any antigen-binding fragment thereof, the bispecific molecule, or the immunoconjugate according to the invention and a pharmaceutically acceptable carrier, excipient or diluent.

In some embodiments the pharmaceutical composition further comprises an adjuvant and in other embodiments the pharmaceutical composition further comprises at least one additional anti-anthrax agent.

The present invention further provides a pharmaceutical composition comprising an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof.

The present invention further provides the isolated monoclonal antibody or any antigen-binding fragment thereof, the bispecific molecule, the immunoconjugate or the pharmaceutical composition according to the invention for use in prophylaxis, treatment or amelioration of *Bacillus anthracis* infection.

By still another one of its aspects the present invention provides an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof for use in prophylaxis, treatment or amelioration of *Bacillus anthracis* infection.

The present invention further provides a method of prophylaxis, treatment or amelioration of *Bacillus anthracis* infection comprising administering to a subject in need thereof a therapeutically effective amount of the isolated monoclonal antibody or any antigen-binding fragment thereof, the bispecific molecule, the immunoconjugate or the pharmaceutical composition according to the invention.

In some embodiments the method or use in accordance with the invention further comprises administering to a subject in need thereof at least one additional anti-anthrax agent.

By yet another one of its aspects, the present invention provides a method of prophylaxis, treatment or amelioration of *Bacillus anthracis* infection comprising administering to a subject in need thereof a therapeutically effective amount of an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof.

In some embodiments the isolated monoclonal antibody or any antigen-binding fragment thereof, the bispecific molecule, the immunoconjugate or the pharmaceutical composition is administered to said subject prior to or after infection with *Bacillus anthracis*.

In other embodiments the isolated monoclonal antibody or any antigen-binding fragment thereof, the bispecific molecule, the immunoconjugate or the pharmaceutical composition is administered to said subject prior or immediately after *Bacillus anthracis* infection or between about 1 to about 30 days after *Bacillus anthracis* infection.

In further embodiments the antibody is administered at a therapeutically effective amount of 0.01 to 100 mg/kg.

In still further embodiments the isolated monoclonal antibody or any antigen-binding fragment thereof, the bispecific molecule, the immunoconjugate or the pharmaceutical composition as herein defined is administered to said subject as a single dose or as multiple doses.

Still further the present invention provides a method of neutralizing *Bacillus anthracis* toxicity comprising administering to a subject in need thereof a therapeutically effective amount of the isolated monoclonal antibody or any antigen-binding fragment thereof, the bispecific molecule, the immunoconjugate or the pharmaceutical composition according to the invention.

By another one of its aspects the present invention provides a kit comprising the isolated monoclonal antibody or any antigen-binding fragment thereof as herein defined and instructions for use.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1: Nucleic acid and amino acid sequences of the heavy and the light chains of the chimeric antibody cAb 29 and the mutated antibody PA29mut29. Nucleic and amino acid sequences of the heavy chains of cAb 29 and PA29mut29 are denoted by PA29VH w.t. and PA29mut29VH, respectively and nucleic and amino acid sequences of the light chains of cAb 29 and PA29mut29 are denoted by PA29VL w.t. and PA29mut29VL, respectively. Mutated nucleotides and amino acid residues are indicated by bold underlined letters.

FIG. 2: Nucleic acid and amino acid sequences of the heavy and the light chains of the mutated antibodies PA29mut33 and PA29mut39. Nucleic and amino acid sequences of the heavy chains of PA29mut33 and PA29mut39 are denoted by PA29mut33VH and PA29mut39VH, respectively and nucleic and amino acid sequences of the light chains of PA29mut33 and PA29mut39 are denoted by PA29mut33VL and PA29mut39VL, respectively. Mutated nucleotides and amino acid residues are indicated by bold underlined letters.

FIG. 3: Nucleic acid and amino acid sequences of the heavy and the light chains of the mutated antibodies PA29mut40 and PA29mut41. Nucleic and amino acid sequences of the heavy chains of PA29mut40 and PA29mut41 are denoted by PA29mut40VH and PA29mut41VH, respectively and nucleic and amino acid sequences of the light chains of PA29mut40 and PA29mut41 are denoted by PA29mut40VL and PA29mut41VL, respectively. Mutated nucleotides and amino acid residues are indicated by bold underlined letters.

FIGS. 4A-4C: Multiple sequence alignment of the heavy chain variable domains of the wild type and mutated antibodies. Sequence alignment of the heavy chain variable domains of the wild type and mutated antibodies are presented for fragments comprising the complementarity determining regions (CDR) CDRH1 (FIG. 4A), CDRH2 (FIG. 4B) and CDRH3 (FIG. 4C). CDRs are shown in grey boxes and the mutated amino acid residues are indicated by bold underlined letters. Abbreviations: w.t., cAb 29; 29, PA29mut29; 33, PA29mut33; 39, PA29mut39; 40, PA29mut40; and 41, PA29mut41.

FIGS. 5A-5C: Multiple sequence alignment of the light chain variable domains of the wild type and mutated antibodies. Sequence alignment of the light chain variable domains of the wild type and mutated antibodies are presented for fragments comprising the complementarity determining regions (CDR) CDRL1 (FIG. 5A), CDRL2 (FIG. 5B) and CDRL3 (FIG. 5C). CDRs are shown in grey boxes and the mutated amino acid residues are indicated by bold underlined letters. Abbreviations: w.t., cAb 29; 29, PA29mut29; 33, PA29mut33; 39, PA29mut39; 40, PA29mut40; and 41, PA29mut41.

DETAILED DESCRIPTION OF EMBODIMENTS

The present invention is based on the sequencing and characterization of specific antibodies directed to *Bacillus anthracis* protective antigen (PA), in particular a chimeric antibody, and variants thereof harboring specific amino acid substitutions in the sequence of the heavy chain and the light chain of the antibody.

The present invention thus provides an isolated monoclonal antibody or any antigen-binding fragment thereof which binds to *Bacillus anthracis* protective antigen, wherein the antibody comprises a heavy chain variable region comprising:

a) the complementarity determining region CDRH1 comprising the amino acid sequence of IFTNYNMH denoted by SEQ ID NO. 3 or a variant thereof;

b) the complementarity determining region CDRH2 comprising the amino acid sequence AIYPRTGDTSYN-QKFKG denoted by SEQ ID NO. 4 or a variant thereof; and c) the complementarity determining region CDRH3 comprising the amino acid sequence ARDGFAY denoted by SEQ ID NO. 5 or a variant thereof; and a light chain variable region comprising:

d) the complementarity determining region CDRL1 comprising the amino acid sequence RASQDISNYLN denoted by SEQ ID NO. 8 or a variant thereof;

e) the complementarity determining region CDRL2 comprising the amino acid sequence YTSRLHS denoted by SEQ ID NO. 9 or a variant thereof; and f) the complementarity determining region CDRL3 comprising the amino acid sequence QQGKTLPWT denoted by SEQ ID NO. 10 or a variant thereof.

The term "*Bacillus anthracis*" (or "*B. anthracis*") as herein defined refers to a Gram-positive, endospore-forming rod-shaped bacterium that can be grown in an ordinary nutrient medium under aerobic or anaerobic conditions. The bacterium can form dormant soil-borne endospores (often referred to as "spores") that are able to survive in harsh conditions for decades. When spores are inhaled, ingested, or come into contact with a skin lesion on a host, they may become reactivated and multiply rapidly.

As known in the art, the disease Anthrax is an acute disease caused by the bacterium *Bacillus anthracis*. Most forms of the disease are lethal, and it affects both humans and animals.

Anthrax toxin is a three-protein exotoxin secreted by *Bacillus anthracis*. Anthrax toxin is composed of a cell-binding protein, known as protective antigen (PA), and two enzyme components, edema factor (EF) and lethal factor (LF). PA, EF and LF act together to impart their physiological effects.

Assembled complexes containing the toxin components are endocytosed. In the endosome, the enzymatic components of the toxin translocate into the cytoplasm of a target cell. Once in the cytosol, the enzymatic components of the toxin disrupt various cell functions, namely cellular signaling and cell migration. Anthrax toxin ultimately allows the bacteria to evade the immune system, proliferate, and ultimately kill the host.

"Protective antigen" (PA) as herein defined refers to the central component of the three-part protein toxin secreted by *Bacillus anthracis*. After proteolytic activation on the host cell surface, PA forms a membrane-inserting heptamer that translocates the toxic enzymes, edema factor (EF) and lethal factor (LF), into the cytosol.

*B. anthracis* PA may be prepared by any method known in the art. For example, from the *B. anthracis* strain V770-NPI-R, anaerobically grown as previously described (10). Briefly, bacteria are grown at 37° C. in Luria-Bertani (LB) medium supplemented with 25 µg/ml kanamycin. After 24 hours of growth, bacteria is removed by microfiltration, while the protective antigen (PA) containing supernatant is concentrated by ultrafiltration and dialyzed against 20 mM phosphate buffer (pH=8.0). Purification of PA may be carried out by Q-Sepharose chromatography, essentially as previously described (11).

As indicated above, the present invention provides defined isolated monoclonal antibodies that bind to *Bacillus anthracis* protective antigen. The term "antibody" refers to a polypeptide that generally contains heavy chain polypeptides and light chain polypeptides and is encoded by an immunoglobulin gene, or functional fragments thereof that specifically bind and recognize an antigen, namely *Bacillus anthracis* PA.

An antibody as herein defined comprises one of five different types of heavy chains, called alpha, delta, epsilon, gamma, and mu, based on the amino acid sequence of the heavy chain constant region. These different types of heavy chains give rise to five classes of antibodies, IgA (including IgA1 and IgA2), IgD, IgE, IgG (IgG1, IgG2, IgG3, and IgG4) and IgM, respectively. An antibody also comprises one of two types of light chains, called kappa or lambda, based on the amino acid sequence of the light chain constant domains.

The term "monoclonal antibody", "monoclonal antibodies" or "mAb" as herein defined refers to a population of substantially homogenous antibodies, namely, the individual antibodies comprising the population are identical except for possibly naturally occurring mutations that may be present in minor amounts. Monoclonal antibodies are directed against a single antigenic site.

Monoclonal antibodies may be prepared and purified by any method known in the art. For example, monoclonal antibodies may be prepared from B cells taken from the spleen or lymph nodes of immunized animals (e.g. rats or mice), by fusion with immortalized B cells under conditions which favor the growth of hybrid cells.

Immunization of mice for the preparation of monoclonal antibodies may be carried out by primary sub-cutaneous (s.c.) immunization using PA (e.g. 50 µg) emulsified with complete Freund's adjuvant. Two subcutaneous booster injections with PA (e.g. 50 µg) emulsified with incomplete Freund's adjuvant are then administered every 2 weeks. The mice with the highest neutralizing antibody titer receive an additional intravenous (i.v.) boost of PA (e.g. 5 µg) in PBS four days prior to spleen removal.

After the final boost (e.g. four days), the spleen of the mouse with the highest neutralizing antibody titer is removed and splenocytes are fused to mouse myeloma cells (e.g. NS0 cells) using polyethylene glycol, as previously described (12). After fusion, the hybridoma cells are selected by growing the cells in HAT (hypoxantine-aminopterin-thymidine) medium. Cell clones are then screened for neutralizing antibody production, for example using the direct and indirect ELISA assays described below.

Antibodies may also be prepared using phage display. As known in the art, antibody phage display (APD) is based on genetic engineering of bacteriophages and repeated rounds of antigen-guided selection and phage propagation.

The APD process begins with antibody-library preparation, by preparation of quality RNA from the cell source chosen (e.g., peripheral blood mononuclear cells). This RNA is reverse-transcribed into cDNA, which is used for PCR of the VH and VL chains of the encoded antibodies. This step is followed by ligation of the variable heavy (VH) and variable light (VL) PCR products into a phage display vector, culminating in analysis of clones of mAbs.

Purification of monoclonal antibodies may be based for example on affinity chromatography, namely, using an affinity column to which a specific epitope is conjugated.

Binding to *Bacillus anthracis* protective antigen by the antibodies prepared according to the present disclosure may be examined by any method known to a person skilled in the art, for example using the direct and indirect ELISA assays described below.

An exemplary IgG antibody structural unit comprises a tetramer, as known in the art. Each tetramer is composed of two identical pairs of polypeptide chains, each pair having one "light chain" and one "heavy chain". The N-terminus of each chain defines a variable region of about 100 to 110 or more amino acids primarily responsible for antigen (or epitope) recognition.

Thus, the terms "heavy chain variable region" ($V_H$) and "light chain variable region" ($V_L$) refer to these heavy and light chains, respectively. More specifically, the variable region is subdivided into hypervariable and framework (FR) regions. Hypervariable regions have a high ratio of different amino acids in a given position, relative to the most common amino acid in that position. Four FR regions which have more stable amino acids sequences separate the hypervariable regions. The hypervariable regions directly contact a portion of the antigen's surface. For this reason, hypervariable regions are herein referred to as "complementarily determining regions", or "CDRs".

From N-terminal to C-terminal, both light and heavy chains comprise the regions (also referred to as domains) FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located (namely the heavy or the light chain).

Thus, the complementarity determining regions CDRH1, CDRH2 and CDRH3 refer to the three complementarity determining regions starting from the N-terminus of the antibody's heavy chain and the complementarity determining regions CDRL1, CDRL2 and CDRL3 refer to the three complementarity determining regions starting from the N-terminus of the antibody's light chain.

As detailed above the present invention provides an isolated monoclonal antibody, which comprises a heavy chain variable region comprising the CDRH1 comprising the amino acid sequence of IFTNYNMH denoted by SEQ ID NO. 3 or a variant thereof, the CDRH2 comprising the amino acid sequence AIYPRTGDTSYNQKFKG denoted by SEQ ID NO. 4 or a variant thereof, and the CDRH3 comprising the amino acid sequence ARDGFAY denoted by SEQ ID NO. 5 or a variant thereof; and a light chain variable region comprising: the CDRL1 comprising the amino acid sequence RASQDISNYLN denoted by SEQ ID NO. 8 or a variant thereof; the CDRL2 comprising the amino acid sequence YTSRLHS denoted by SEQ ID NO. 9 or a variant thereof; and the CDRL3 comprising the amino acid sequence QQGKTLPWT denoted by SEQ ID NO. 10 or a variant thereof.

The above CDR sequences CDRH1, CDRH2, CDRH3, CDRL1, CDRL2 and CDRL3 denoted by SEQ ID NO. 3, SEQ ID NO. 4, SEQ ID NO. 5, SEQ ID NO. 8, SEQ ID NO. 9 and SEQ ID NO. 10 (Table 1), respectively are also presented in the context of their respective heavy and light chains sequences, e.g. in FIGS. 4A-4C and in FIGS. 5A-5C.

For example, the sequence of CDRH1, denoted herein by SEQ ID NO. 3, is shown in FIG. 4A in a grey box, for each of the antibodies described below.

As shown in the accompanying examples, various mutated antibodies of the antibody cAb29 were prepared and shown to bind *Bacillus anthracis* protective antigen.

Thus the present invention also encompasses variants (also referred to herein as "mutated antibodies") of the heavy and light chain variable regions. The variants may include mutations in the complementarity determining regions of the heavy and light chains, or in the framework regions, which do not alter the biological activity of the antibodies herein described (namely binding to *Bacillus anthracis* PA).

By the term "variant" it is meant sequences of amino acids or nucleotides different from the sequences specifically identified herein, in which one or more amino acid residues or nucleotides are deleted, substituted or added.

It should be appreciated that by the term "added", as used herein it is meant any addition(s) of amino acid residues to the sequences described herein. For example, the variant antibodies or fragments thereof of the invention may be extended at their N-terminus and/or C-terminus with various identical or different amino acid residues.

Variants encompass various amino acid substitutions. An amino acid "substitution" is the result of replacing one amino acid with another amino acid which has similar or different structural and/or chemical properties Amino acid substitutions may be made on the basis of similarity in polarity, charge, solubility, hydrophobicity, hydrophilicity, and/or the amphipathic nature of the residues involved.

Surprisingly, as shown in the appended Examples, certain variants according to the invention had similar (or higher) binding affinity to their PA ligand as compared to the original antibody, where an uncharged polar amino acid was replaced by a charged polar amino acid (Glutamine to Glutamic acid and Glutamine to Arginine in the antibody PA29mut33) and where a polar amino acid was replaced by a non-polar amino acid (Serine to Proline in the antibody PA29mut40 and Glutamic acid to Glycine in the antibody PA29mut29). Therefore variants in accordance with the invention encompass inter alia non-polar to polar amino acid substitutions and vice-versa.

Variants also encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acids sequences that may be characterized by the percentage of the identity of their amino acid or nucleotide sequences with the amino acid or nucleotide sequences described herein (namely the amino acid or nucleotide sequences of the heavy and light chains of the antibodies herein described).

In some embodiments, variant sequences as herein defined refer to nucleic acid sequences that encode the heavy and light chain variable regions, each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the sequences of the heavy and light chain variable regions described herein.

In some embodiments the isolated monoclonal antibody according to the invention is wherein its heavy chain variable region is encoded by a nucleic acid sequence which is at least 70% identical to the nucleic acid sequence of the heavy chain variable region denoted by SEQ ID NO. 1 and wherein its light chain variable region is encoded by a nucleic acid sequence which is at least 70% identical to the nucleic acid sequence of the light chain variable region denoted by SEQ ID NO. 6.

By the term "biological activity" it is meant the ability of the antibody to neutralize the toxicity of *Bacillus anthracis*.

As reported by Mechaly, A. et al. (8), incorporated herein by reference, numerous PA-neutralizing monoclonal antibodies directed against all the four domains of PA were isolated and described to date Interestingly, the antibodies in accordance with the invention are able to bind to *B. anthracis* PA at any stage of PA intoxication and specifically, to neutralize *B. anthracis* PA intoxication by inhibiting the prepore-to-pore conversion step.

Without wishing to be bound by theory, this unique neutralizing activity of the antibody in accordance with the invention provides the antibodies described herein with a broad range of neutralizing activity and in particular with the ability to prevent the translocation of LF (or EF) into the cell. It can therefore be hypothesized that antibodies that bind to the heptamer form of PA, even when it has already bound LF/EF and inhibit the last stage of intoxication, namely, receptor binding, internalization and pore formation, will provide superior protection against anthrax as compared to other antibodies directed to other epitopes in PA.

The ability of the antibody to neutralize the toxicity of *B. anthracis* may be monitored by any method known in the art, in particular, using the methods described herein below. These methods include but are not limited to in vitro LeTx neutralization assay, namely by assessing the ability of the antibody to protect murine macrophage J774A.1 cells against PA/LF toxin complex (LeTx) intoxication (11). Briefly, tested antibody samples are serially diluted by two-fold dilutions in a buffer containing PA (5 μg/ml) and LF (2 μg/ml), and after one hour of incubation, 10 μl of each of the reaction mixture dilutions is added to J774A.1 cells. Plates are then incubated for 5 hours at 37° C. in 5% $CO_2$, and cell viability is monitored by the MTT (3-[4,5-Dimethylthiazol-2-yl]-2,5-Diphenyltetrazolium bromide; Thiazolyl blue) assay, reflecting the number of viable cells (13).

The ability of the antibody to neutralize the toxicity of *B. anthracis* may also be monitored by in vivo neutralization experiments in animals subjected to LeTx challenge, for example as detailed below.

LeTx challenge in rats consists of evaluating the ability of the antibody to protect rats against a LeTx challenge. To this end, rats (e.g. Male Fisher 344) are injected intramuscularly (i.m.) with various doses of antibodies. Seventeen hours later, rats are anesthetized with ketamine:xylazine (50:2 mg/kg) and injected via the tail vein (i.v.) with LeTx, containing 20 μg PA and 10 μg LF in 500 μl saline, and monitored for survival.

The ability of the antibody to protect against anthrax spore challenge may also be performed in guinea pigs, by injecting guinea pigs i.m. with various doses of antibodies, and 14 hrs later challenging by subcutaneous (s.c.) administration of 40 $LD_{50}$ anthrax Vollum spores as described previously (10). Animal viability is then monitored for at least 14 days.

Additional in vitro experiments for determining the binding of the antibody prepared according to the invention to its target protein include for example direct and indirect-ELISA assays.

Direct-ELISA assay for anti-PA antibody titration can be performed in 96-well microtiter plates using an RMP200 (TECAN, Switzerland) robotic system. PA is used as the capture antigen and a suitable alkaline phosphatase-conjugated secondary antibody may be used for detection. Indirect-ELISA may be performed using Rabbit anti-PA as the capture antibody for PA.

As indicated above, the present invention is based on the identification of a specific chimeric antibody directed to *Bacillus anthracis* protective antigen (PA), and variants thereof (referred to below as "mutated antibodies"). As detailed below, the antibody of the invention comprises heavy and light chains having the amino acid sequences denoted by SEQ ID NO. 2 and SEQ ID NO. 7, respectively (the sequences are shown for example in Table 1).

Thus in some embodiments the isolated monoclonal antibody according to the invention is wherein its heavy chain variable region is of the amino acid sequence denoted by SEQ ID NO. 2 or a variant thereof.

In some embodiments, the present invention pertains to an isolated monoclonal antibody or any antigen-binding fragment thereof, wherein the antibody comprises a heavy chain variable region in which at least one amino acid residue is replaced or substituted with respect to the amino acid sequence of the heavy chain variable region denoted by SEQ ID NO. 2.

As demonstrated below, the variant antibodies PA29mut33 and PA29mut41 were shown to bind *Bacillus anthracis* protective antigen.

Thus in some embodiments the isolated monoclonal antibody according to the invention is wherein its heavy chain variable region comprises a substitution in at least one position selected from the group consisting of position 1 and position 16 of SEQ ID NO. 2.

By the term "position" it is meant the location within the amino acid sequence, where "position 1" indicates the N-terminal amino acid residue, "position 2" indicates the amino acid residue that is adjacent to the N-terminal amino acid residue and so forth in the direction of N-terminal to C-terminal, as known in the art.

For example, in the amino acid sequence of the heavy chain variable region of the antibody of the invention, denoted by SEQ ID NO. 2 (Table 1), "position 1" refers to the N-terminal amino acid residue, namely glutamine (Gln, Q), "position 2" refers to valine (Val, V), and "position 16" refers to alanine (Ala, A), etc.

In some embodiments the isolated monoclonal antibody according to the invention comprised the heavy chain variable region of the variant antibody PA29mut33, namely wherein its heavy chain variable region comprises the amino acid residue glutamic acid (Glu, E) at position 1 of SEQ ID NO. 2 and wherein said heavy chain variable region is of the amino acid sequence denoted by SEQ ID NO. 16.

In other embodiments the isolated monoclonal antibody according to the invention comprised the heavy chain variable region of the variant antibody PA29mut41, namely wherein its heavy chain variable region comprises the amino acid residue valine (Val, V) at position 16 of SEQ ID NO. 2 and wherein said heavy chain variable region is of the amino acid sequence denoted by SEQ ID NO. 28.

As indicated above, the antibody of the invention comprises heavy and light chains having the amino acid sequences denoted by SEQ ID NO. 2 and SEQ ID NO. 7, respectively.

Thus in some embodiments the isolated monoclonal antibody according to the invention is wherein its light chain variable region is of the amino acid sequence denoted by SEQ ID NO. 7 or a variant thereof.

As demonstrated below, the variant antibodies PA29mut29, PA29mut39 and PA29mut40 were also shown to bind *Bacillus anthracis* protective antigen.

Thus in some embodiments the isolated monoclonal antibody according to the invention is wherein its light chain variable region comprises a substitution in at least one position selected from the group consisting of position 3, 9, 21, 57 and 87 of SEQ ID NO. 7.

In other words, the invention encompasses an isolated monoclonal antibody in which at least one of the amino acid residues glutamine at position 3, serine at position 9, isoleucine at position 21, glutamic acid at position 57 and phenylalanine at position 87 of SEQ ID NO. 7 is substituted by another amino acid.

In some embodiments the isolated monoclonal antibody according to the invention comprises the light chain variable region of the variant antibody PA29mut33, namely wherein its light chain variable region comprises the amino acid residue arginine (Arg, R) at position 3 of SEQ ID NO. 7 and wherein said light chain variable region is of the amino acid sequence denoted by SEQ ID NO. 18.

In other embodiments the isolated monoclonal antibody according to the invention comprises the light chain variable region and the heavy chain variable region of the variant antibody PA29mut33, denoted by SEQ ID NO. 18 and SEQ ID NO. 16, respectively.

In further embodiments the isolated monoclonal antibody according to the invention comprises the light chain variable region of the variant antibody PA29mut40, namely wherein its light chain variable region comprises the amino acid residue proline (Pro, P) at position 9 of SEQ ID NO. 7 and wherein said light chain variable region is of the amino acid sequence denoted by SEQ ID NO. 26.

In still further embodiments the isolated monoclonal antibody according to the invention comprises the light chain variable region of the variant antibody PA29mut39, namely wherein its light chain variable region comprises the amino acid residue valine (Val, V) at position 21 of SEQ ID NO. 7 and wherein said light chain variable region is of the amino acid sequence denoted by SEQ ID NO. 22.

In other embodiments the isolated monoclonal antibody according to the invention comprises the light chain variable region of the variant antibody PA29mut29, namely wherein its light chain variable region comprises the amino acid residue glycine (Gly, G) at position 57 and the amino acid residue tyrosine (Tyr, Y) at position 87 of SEQ ID NO. 7 and wherein said light chain variable region is of the amino acid sequence denoted by SEQ ID NO. 14.

In specific embodiments the isolated monoclonal antibody according to the invention is wherein said heavy chain variable region is of the amino acid sequence denoted by SEQ ID NO. 2 and wherein said light chain variable region is of the amino acid sequence denoted by SEQ ID NO. 7.

In specific embodiments of the present disclosure the isolated monoclonal antibody comprises the light chain variable region and the heavy chain variable region of the variant antibody PA29mut29, denoted by SEQ ID NO. 14 and SEQ ID NO. 12, respectively.

In other specific embodiments of the present disclosure the isolated monoclonal antibody comprises the light chain variable region and the heavy chain variable region of the variant antibody PA29mut39, denoted by SEQ ID NO. 22 and SEQ ID NO. 20, respectively.

In further specific embodiments of the present disclosure the isolated monoclonal antibody comprises the light chain variable region and the heavy chain variable region of the variant antibody PA29mut40, denoted by SEQ ID NO. 26 and SEQ ID NO. 24, respectively.

In still further specific embodiments of the present disclosure the isolated monoclonal antibody comprises the light chain variable region and the heavy chain variable region of the variant antibody PA29mut41, denoted by SEQ ID NO. 30 and SEQ ID NO. 28, respectively.

In some embodiments the isolated monoclonal antibody according to the invention is a chimeric, a humanized or a human antibody.

In one embodiment, the antibody of the invention is a chimeric antibody containing mouse variable region genes ($V_H$ and $V_L$) fused to human constant region genes (Cγ1 and Cκ, respectively).

The term "chimeric" antibodies as herein defined refers to antibodies in which a portion of the heavy and/or light chain is derived from a particular species, while the remainder of the chain(s) is derived from another species, as well as fragments of such antibodies, which exhibit the same biological activity.

Chimeric antibodies may be prepared by any method known in the art, for example as described below.

A murine-human chimeric antibody may be prepared by the amplification and cloning of murine $V_H$ and $V_L$ genes, encoding the antibody variable regions, followed by murine-human chimeric antibody expression. To this end, total RNA is isolated from the murine anti-PA hybridoma cells that are shown to secrete antibodies with the desired characteristics and cDNA is synthesized using oligo $(dT)_{15}$ primer, M-MLV and AMV reverse transcriptases Amplification of the heavy and the light variable genes (VH and $V_L$) may be carried out using a panel of primers directed at the 5' terminus of framework 1 of each gene, essentially as described in Benhar, I. et al. (14), and to the constant region ($C_H1$ or $C_k$, respectively) at the 3' end.

The variable genes are then re-amplified using non-degenerate primers introducing restriction sites at both ends for cloning into a pCMV-based antibody expression vector as described for example in Rosenfeld et al (7), incorporated herein by reference.

The amplified heavy and light variable genes are separately purified, digested and cloned into appropriate mammalian (human) full-length Ig expression vectors, providing each chain with a corresponding signal-peptide and constant gene, resulting in IgG1/k murine human chimeric antibody expression.

For preparing large quantities of the antibody, a stable cell line expressing the antibody can be prepared, by transfecting cells (e.g. CHO cells) with the Ig expression vector containing both heavy and light chains of the chimeric antibody. Highly anti-PA antibody producing clones may be then selected and expanded based on antibody levels in the supernatant, as tested by any method known in the art, for example, PA-specific ELISA assay, as detailed herein.

By another one of its aspects the present invention provides an isolated chimeric antibody, or any antigen-binding fragment thereof which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof.

In a further specific aspect the present invention provides an isolated chimeric murine-human antibody, or any antigen-binding fragment thereof which binds to *Bacillus anthracis* protective antigen, wherein the antibody comprises a heavy chain variable region of the amino acid sequence denoted by SEQ ID NO. 2 and a light chain variable region of the amino acid sequence denoted by SEQ ID NO. 7.

It is appreciated that "humanized" forms of non-human (for example, murine) antibodies are antibodies that contain a human-derived immunoglobulin framework with minimal sequences derived from non-human immunoglobulin at the CDRs and optionally at additional relevant positions. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and activity.

The term "human antibody" as used herein refers to an antibody that possesses an amino acid sequence corresponding to that of an antibody produced by a human and/or has been made using any of the techniques for making human antibodies disclosed herein. This definition specifically excludes a humanized antibody that comprises non-human antigen-binding residues.

Preparation of humanized and human antibodies is well known in the art.

The present invention further encompasses any antigen-binding fragments of the isolated monoclonal antibody of the invention.

The term "antigen-binding fragments" in the context of the isolated monoclonal antibody of the present disclosure refer to a polypeptide derived from an antibody polypeptide molecule that does not comprise a full-length antibody polypeptide, but that still comprises at least a portion of a full-length antibody polypeptide that is capable of binding to an antigen.

Such antigen-binding fragments may include for example fragment antigen-binding (Fab) and F(ab')$_2$, which are capable of binding antigen. Such fragments may be produced by any method known in the art, for example by proteolytic cleavage, using enzymes such as papain (to produce Fab fragments) or pepsin (to produce F(ab')$_2$ fragments). Other examples of antigen-binding fragments encompassed herein are variable fragment (Fv), single chain variable fragment Fv (scFv) and linear antibodies. Additional examples of antigen-binding antibody fragments are known in the art.

Thus in some embodiments the isolated monoclonal antibody according to the invention is wherein said antibody is an antibody fragment selected from the group consisting of Fv, single chain Fv (scFv), heavy chain variable region, light chain variable region, Fab, F(ab)$_2$' and any combination thereof.

Rosenfeld et al. (7), incorporated herein by reference, describe the generation of antibodies directed against the complete PA protein. Of the 600 hybridoma cell lines obtained from a single fusion process, 101 clones displayed PA-neutralizing activities at different levels. The monoclonal antibody termed mAb 29 demonstrated the highest neutralizing activity. A chimeric antibody (cAb 29) based on mAb 29 was produced.

cAb29 was shown to neutralize PA-LF complex (LeTx) activity in vitro in the J774A macrophage cell line, and in vivo in a LeTx challenge performed in rats (7) and was also shown to confer full protection to guinea pigs when given prior to infection with 40 LD$_{50}$ B. anthracis spores and to protect all infected rabbits, when treated 12 hours post exposure (200 LD$_{50}$) as shown by Rosenfeld R. et al. and Mechaly, A., et al., the content of which is incorporated herein by reference (7, 8).

Briefly, in the LeTx challenge performed in rats, antibodies were administered intramuscularly (i.m.) at different doses, followed by an intravenous (i.v.) challenge with a lethal dose of LeTx.

A dose of 170 μg/kg cAb 29 was needed in order to provide 50% protection (PD$_{50}$).

In the guinea pig protection assay, antibody at doses of either 5, 10 or 20 mg/kg were administered intramuscularly (i.m.) to guinea pigs 14 hrs prior to challenge with 40LD$_{50}$ of B. anthracis Vollum spores. Under these challenge conditions, control animals (which did not receive treatment) died within 3 days post infection, with Mean Time to Death (MTTD) of 2.5 days.

However, when treated with antibody at a dose of 5 mg/kg, 50% of the guinea pigs survived the challenge with a delayed MTTD of 7 days, significantly longer (P<0.005) than the respective control group value.

The efficacy of cAb29 as post exposure therapy was evaluated in rabbits that were intranasally infected with 5×10$^6$ cfu of Vollum spores (200 LD$_{50}$). In this assay, the antibody was administered to rabbits in two successive treatments, given 12 and 60 hours after infection. All the animals treated twice with 1 mg/kg survived the challenge with no evident disease within 14 days after challenge.

In addition, endogenous immune response against PA was developed in infected guinea pigs treated with cAb 29 and this immune response conferred protection against anthrax re-challenge.

The ability of cAb 29 to confer endogenous protective immunity against B. anthracis re-challenge as described above, along with the protective effect demonstrated for cAb29 pre- and post exposure to B. anthracis, suggest that cAb 29 is a potent antibody for the prophylaxis and treatment of B. anthracis infection.

Thus in some embodiments the isolated monoclonal antibody according to the invention is a neutralizing antibody.

The term "Neutralizing antibody" (or Nab) as herein defined refers to an antibody which defends a cell from an antigen or infectious body by inhibiting or neutralizing the biological effect of the antigen or infectious body. Neutralizing antibodies are mainly defined by their in vitro activity, which in the present case may be assessed by their inhibition of PA-LF toxin complex-mediated cell-death (LeTx assay). It has previously been shown that the results of the LeTx assay can serve as a surrogate marker to predict an antibody's neutralization potential against anthrax challenges in vivo (11). The typical method for elucidating the PA-neutralizing capacity of monoclonal antibodies includes a wide screen and the selection of antibodies that bind to adsorbed PA (using for example a direct ELISA format), and only then the best binders are further screened for their ability to neutralize PA in the LeTx assay.

The present invention further provides a bispecific molecule comprising the antibody according to the invention.

The term "bispecific molecule" as herein defined comprises an antibody or any antigen binding fragment thereof as herein defined and a second entity, preferably a second antibody or antigen binding fragment thereof that specifically binds a different target, such as but not limited to an epitope in Bacillus anthracis that is different from the epitope recognized by the antibodies in accordance with the invention. The second antibody or antigen binding fragment thereof may target toxins of Bacillus anthracis (e.g EF or LF), any other protein of another pathogen, host-related protein, or host cell as non-limiting examples. Bispecific antibodies include cross-linked or "heteroconjugate" antibodies and can be made using any convenient cross-linking or recombinant methods.

In another one of its aspects the present invention provides an isolated nucleic acid molecule comprising a nucleotide sequence encoding an antibody or any antigen-binding fragment thereof according to the invention.

The term "nucleic acid" or "nucleic acid molecule" as herein defined refers to polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

The invention further provides an expression vector comprising the isolated nucleic acid molecule as herein defined.

"Expression vector" sometimes referred to as "expression vehicle" or "expression construct", as used herein, encompass vectors such as plasmids, viruses, bacteriophage, integratable DNA fragments, and other vehicles, in which another polynucleotide segment is attached, resulting in the replication and/or expression of the attached segment and which in some cases enable the integration of DNA fragments into the genome of the host.

Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few. For example, the expression vector may be pCMV-based antibody expression vector, as exemplified herein below.

In yet another one of its aspects the present invention provides a host cell transfected with the isolated nucleic acid molecule according to the invention or with the expression vector according to the invention.

The term "host cells" as used herein refers to cells which are susceptible to the introduction of the isolated nucleic acid molecule according to the invention or the expression vector according to the invention. Preferably, said cells are mammalian cells, for example CHO cells, HEK 293. Transfection of the isolated nucleic acid molecule or the expression vector according to the invention to the host cell may be performed by any method known in the art.

In yet another one of its aspects the present invention provides an immunoconjugate comprising the antibody or any antigen-binding fragment thereof according to the invention and an additional anti-anthrax agent.

The term "immunoconjugate" as herein defined refers to an antibody or any antigen-binding fragment thereof according to the invention that is conjugated (linked or joined) to an additional agent Immunoconjugates may be prepared by any method known to a person skilled in the art, for example, by cross-linking the additional agent to the antibody according to the invention or by recombinant DNA methods.

The term "additional anti-anthrax agent" used herein refers to any agent that may be used for the identification or prophylaxis, treatment or amelioration of *B. anthracis* infection. In some embodiments the additional anti-anthrax agent in accordance with the invention is a cytotoxic agent (e.g. a toxin, an anti-metabolite), an antibiotic agent, a radioactive label (e.g. $H^3$, $I^{125}$, $S^{35}$, $C^{14}$, $P^{32}$) antitoxin therapies or an additional antibody.

The antibiotic agent that may be used in conjunction with the antibody as herein defined is any antibiotic agent that is known in the art to affect infection by *Bacillus anthracis* (e.g. ciprofloxacin, doxycycline, penicillin G procaine, amoxicillin, ofloxacin and levofloxacin).

The term "additional antibody" as herein defined refers to an antibody, which is not the antibody according to the invention, and which may be used in combination with the antibody according to the invention. Such antibody may be directed against *Bacillus anthracis* protective antigen, against a different antigen or toxin of *Bacillus anthracis* (e.g. an antibody that specifically binds *B. anthracis* edema factor, an antibody that specifically binds *B. anthracis* lethal factor), against a different pathogen or against a host-related moiety (e.g an anti TNF-α antibody or an anti IL-1β antibody).

The present invention further provides a pharmaceutical composition comprising as an active ingredient the isolated monoclonal antibody or any antigen-binding fragment thereof, the bispecific molecule according to the invention or the immunoconjugate as herein defined and a pharmaceutically acceptable carrier, excipient or diluents.

The "pharmaceutical composition" of the invention generally comprises the antibody or any antigen-binding fragment thereof as herein defined and a buffering agent, an agent which adjusts the osmolarity of the composition and optionally, one or more pharmaceutically acceptable carriers, excipients and/or diluents as known in the art. Supplementary active ingredients (also referred to herein as additional anti-anthrax agents) can also be incorporated into the compositions, e.g. antibiotics.

As used herein the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

In some embodiments the pharmaceutical composition according to the invention further comprises an adjuvant.

An "adjuvant" as herein defined refers to a pharmacological and/or immunological agent that modifies the effect of other agents. Adjuvants are inorganic or organic chemicals, macromolecules or entire cells of certain killed bacteria, which enhance the immune response to an antigen. Examples of adjuvants include, but are not limited to Freund's adjuvant, aluminium hydroxide etc.

In other embodiments the pharmaceutical composition according to the invention further comprises at least one additional anti-anthrax agent as herein defined.

In specific embodiments the present invention relates to a pharmaceutical composition comprising an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof.

In other specific embodiments the present invention provides a pharmaceutical composition comprising an isolated chimeric antibody, which binds to *Bacillus anthracis* protective antigen, wherein the antibody comprises a heavy chain variable region of the amino acid sequence denoted by SEQ ID NO. 2 and a light chain variable region of the amino acid sequence denoted by SEQ ID NO. 7.

Anthrax is an acute disease as indicated above and therefore the isolated monoclonal antibody or any antigen-binding fragment thereof as herein defined is a potential therapeutic agent against *Bacillus anthracis* infection.

Therefore further provided is a method of prophylaxis, treatment or amelioration of *Bacillus anthracis* infection comprising administering to a subject in need thereof a therapeutically effective amount of the isolated monoclonal antibody or any antigen-binding fragment thereof, the bispecific molecule, the immunoconjugate or the pharmaceutical composition according to the invention.

In some embodiments the invention provides a method of prophylaxis, treatment or amelioration of *Bacillus anthracis* infection comprising administering to a subject in need thereof a therapeutically effective amount of an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof.

By the term "prophylaxis" as herein defined it is meant to provide a "preventive treatment" or "prophylactic treatment", namely acting in a protective manner, to defend against or prevent an infection by *Bacillus anthracis*. In such case a therapeutically effective amount of the isolated monoclonal antibody or any antigen-binding fragment thereof, the bispecific molecule, the immunoconjugate or the pharmaceutical composition as herein defined is administered prior to a potential *Bacillus anthracis* infection.

It is to be understood that the terms "treat", "treating", "treatment" or forms thereof, as used herein, mean preventing, ameliorating or delaying the onset of one or more clinical indications of disease activity resulting from exposure to *Bacillus anthracis* in a subject at risk of being infected or in a subject that was infected by *Bacillus anthracis*.

There are four common routes of anthrax infection, each with different signs and symptoms. Symptoms of cutaneous anthrax include a raised bump that develops into a painless sore with a black center and swelling in the sore and nearby lymph glands; Symptoms of gastrointestinal anthrax include nausea, vomiting, abdominal pain, headache and fever; Symptoms of inhaled anthrax (breathing of anthrax spores) include flu-like symptoms, mild chest discomfort, shortness of breath, nausea, coughing up blood and painful swallowing.

The clinical indications of disease activity resulting from exposure to *Bacillus anthracis* are known to a person skilled in the art, for example a skilled physician.

Administration according to the present invention may be performed by any route known in the art for example by one of the following routes: oral administration, intravenous, intramuscular, intraperitoneal, intratechal or subcutaneous injection; intrarectal administration; intranasal administration, ocular administration or topical administration.

In specific embodiments administration according to the present invention may be performed intravenously.

The antibodies or antibody fragments as herein defined, any pharmaceutical compositions comprising the same or any conjugates comprising them may be administered to a subject prior to or post exposure to *B. anthracis*.

Thus in some embodiments the method of prophylaxis, treatment or amelioration of *Bacillus anthracis* infection according to the invention is where said isolated monoclonal antibody or any antigen-binding fragment thereof, bispecific molmolecule, immunoconjugate or pharmaceutical composition according to the invention is administered to said subject prior to or after infection with *Bacillus anthracis*.

In other embodiments the isolated monoclonal antibody or any antigen-binding fragment thereof, bispecific molecule, immunoconjugate or pharmaceutical composition as herein defined for use in prophylaxis, treatment or amelioration of *Bacillus anthracis* infection is for administration to said subject prior to or after infection with *Bacillus anthracis*.

In specific embodiments the isolated monoclonal antibody or any antigen-binding fragment thereof, bispecific molecule, immunoconjugate or pharmaceutical composition according to the invention is administered to the subject 1, 2, 3, 4, 5, 6 or 7 days, two, three or four weeks, or more before potential exposure to *Bacillus anthracis*, e.g. about a month prior to potential exposure to *Bacillus anthracis*, or immediately after *Bacillus anthracis* infection, or between about 1 to about 30 days or more after *Bacillus anthracis* infection, namely 1, 2, 3, 4, 5, 6 or 7 days, two, three or four weeks, or more after *Bacillus anthracis* infection.

As used herein the term "immediately" encompasses the instant time frame following detection of infection, e.g. minutes or hours after detection.

In some embodiments the method of prophylaxis, treatment or amelioration of *Bacillus anthracis* infection as herein defined further comprises administering to a subject in need thereof at least one additional anti-anthrax agent as herein defined.

In other words, in some embodiments the isolated monoclonal antibody or any antigen-binding fragment thereof, bispecific molecule, immunoconjugate or pharmaceutical composition as herein defined for use according to the invention is adapted for administration to said subject in combination with at least one additional anti-anthrax agent as herein defined.

Administration of the at least one additional anti-anthrax agent may be performed before, concomitantly with or after the administration of the therapeutically effective amount of the isolated monoclonal antibody or any antigen-binding fragment thereof, the bispecific molecule, the immunoconjugate or the pharmaceutical composition as herein defined.

A "therapeutically effective amount" of the isolated monoclonal antibody or any antigen-binding fragment thereof, the bispecific molecule, the immunoconjugate or the pharmaceutical composition according to the invention for purposes herein defined is determined by such considerations as are known in the art in order to cure, arrest or at least alleviate or ameliorate the medical condition associated with *Bacillus anthracis* infection. For any preparation used in the methods of the invention, the dosage or the therapeutically effective amount can be estimated initially from in vitro cell culture assays or based on animal models such as the animal models detailed herein.

Without wishing to be bound by theory, the fact that the antibody in accordance with the invention is active at relatively low doses is the result of its broad activity range and the fact that it interferes with a critical step in PA intoxication.

In some embodiments the therapeutically effective amount in accordance with the invention is in the range of 0.01 to 100 mg/kg of the subject.

In other embodiments the therapeutically effective amount in accordance with the invention is in the range of 0.01 to 40 mg/kg, 0.1 to 40 mg/kg or 1 to 10 mg/kg.

In other embodiments the isolated monoclonal antibody or any antigen-binding fragment thereof, bispecific molecule, immunoconjugate or pharmaceutical composition according to the invention is administered to the subject as a single dose or multiple doses.

The term "subject in need thereof" in the context of the present invention means warm-blooded animals, such as for example rats, mice, dogs, cats, guinea pigs, primates and humans at risk of being exposed to *Bacillus anthracis* (anthrax) or anyone who has come in contact with *Bacillus anthracis* (anthrax) spores, for example veterinarians, laboratory professionals, livestock producers, people who handle animal products, mail handlers, military personnel, and response workers who may be exposed during a bio-terror event involving anthrax spores. Subject in need thereof are also people that were exposed to *Bacillus anthracis*.

The present invention further provides the isolated monoclonal antibody or any antigen-binding fragment thereof according to the invention, the bispecific molecule according to the invention, the immunoconjugate as herein defined or the pharmaceutical composition according to the invention for use in prophylaxis, treatment or amelioration of *Bacillus anthracis* infection.

In specific embodiments the invention provides an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof for use in prophylaxis, treatment or amelioration of *Bacillus anthracis* infection.

Any one of the specific isolated monoclonal antibodies described herein may be used in prophylaxis, treatment or amelioration of *Bacillus anthracis* infection.

Still further the present invention provides use of the isolated monoclonal antibody or any antigen-binding fragment thereof, the bispecific molecule, the immunoconjugate or the pharmaceutical composition according to the invention in the preparation of a medicament for the prophylaxis, treatment or amelioration of *Bacillus anthracis* infection.

In specific embodiments the invention provides use of an isolated chimeric antibody, or any antigen-binding fragment thereof, which binds to *Bacillus anthracis* protective antigen, wherein the antibody comprises a heavy chain variable region of the amino acid sequence denoted by SEQ ID NO. 2 or a variant thereof and a light chain variable region of the amino acid sequence denoted by SEQ ID NO. 7 or a variant thereof in the preparation of a medicament for prophylaxis, treatment or amelioration of *Bacillus anthracis* infection.

As detailed above, the antibodies in accordance with the invention are able to bind to *B. anthracis* PA at any stage of PA intoxication and neutralize *B. anthracis* PA intoxication by inhibiting the prepore-to-pore conversion step.

Thus in still a further aspect the present invention further provide a method of neutralizing *Bacillus anthracis* toxicity comprising administering to a subject in need thereof a therapeutically effective amount of the isolated monoclonal antibody or any antigen-binding fragment thereof according to the invention, the bispecific molecule according to the invention, the immunoconjugate or the pharmaceutical composition according to the invention.

By the term "neutralizing" as herein defined it is meant that by administering to a subject in need thereof a therapeutically effective amount of the isolated monoclonal antibody or any antigen-binding fragment thereof, the bispecific molecule, the immunoconjugate or the pharmaceutical composition according to the invention, the biological effects of *Bacillus anthracis* will be at least partially counteracted, alleviated or ameliorated, as can be monitored by following the subject's clinical symptoms associated with *Bacillus anthracis* infection.

Still further the present disclosure provides the isolated monoclonal antibody or any antigen-binding fragment thereof, the bispecific molecule, the immunoconjugate or the pharmaceutical composition according to the invention for use in neutralizing *Bacillus anthracis* toxicity.

The present disclosure further provides a kit comprising:
(i) an isolated monoclonal antibody or any antigen-binding fragment thereof which binds to *Bacillus anthracis* protective antigen, wherein the antibody comprises a heavy chain variable region comprising:

a) the complementarity determining region CDRH1 comprising the amino acid sequence of IFTNYNMH denoted by SEQ ID NO. 3 or a variant thereof;
b) the complementarity determining region CDRH2 comprising the amino acid sequence AIYPRTGDTSYN-QKFKG denoted by SEQ ID NO. 4 or a variant thereof; and
c) the complementarity determining region CDRH3 comprising the amino acid sequence ARDGFAY denoted by SEQ ID NO. 5 or a variant thereof; and a light chain variable region comprising:
d) the complementarity determining region CDRL1 comprising the amino acid sequence RASQDISNYLN denoted by SEQ ID NO. 8 or a variant thereof;
e) the complementarity determining region CDRL2 comprising the amino acid sequence YTSRLHS denoted by SEQ ID NO. 9 or a variant thereof; and
f) the complementarity determining region CDRL3 comprising the amino acid sequence QQGKTLPWT denoted by SEQ ID NO. 10 or a variant thereof; and
(ii) instructions for use.

It is appreciated that the term "purified" or "isolated" refers to molecules, such as amino acid or nucleic acid sequences, peptides, polypeptides or antibodies that are removed from their natural environment, isolated or separated. An "isolated antibody" is therefore a purified antibody removed from its natural environment. As used herein, the term "purified" or "to purify" also refers to the removal of contaminants from a sample.

As used herein, the term "about", when referring to a measurable value such as an amount, a temporal duration, and the like, is meant to encompass variations of ±10%, more preferably ±5%, even more preferably ±1%, and still more preferably ±0.1% from the specified value, as such variations are appropriate to perform the disclosed invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Example 1

Sequencing and Characterization of a Chimeric Antibody Directed to *B. anthracis* PA A chimeric antibody, also termed herein cAb 29, containing murine variable region genes ($V_H$ and $V_L$) fused to human constant region genes (Cγ1 and Cκ, respectively) was constructed as described in Rosenfeld et al (7). The antibody was introduced into a mammalian expression-system and the recombinant antibody was stably produced by CHO cells.

The chimeric Ab 29 (cAb 29) was sequenced using the ABI 310 Genetic Analyser (Applied Biosystems). The nucleic acid and amino acid sequences of the heavy and the light chains of cAb 29 as well as of the complementarity determining regions (CDRs) of cAb 29 are detailed in Table 1 below.

TABLE 1

Sequences of heavy and light chains and CDRs of cAb29

| SEQ ID NO. | Sequence | Description |
| --- | --- | --- |
| 1 | CAGGTTCAACTGCAGCAGTCTGGGGCTGAGCTGGTGAAGCCT GGGGCCTCAGTGAAGATGTCCTGCAAGGCTTCTGGCTACATA TTTACCCATTACAATATGCACTGGGTACAGCAGACACCTGGA CAGGGCCTGGAATGGATTGGCGCTATTTATCCACGAACTGGT GATACTTCCTACAATCAGAAGTTCAAAGGCAAGGCCACATTG ACTGCAGACAAATCCTCCAGCACAGCCTACATGCAGCTCAGC AGCCTGACATCTGAGGATTCTGCGGTCTATTACTGTGCAAGA GACGGGTTTGCTTACTGGGGCCAAGGG | Nucleic acid sequence of the heavy chain variable region ($V_H$) |
| 2 | QVQLQQSGAELVKPGASVKMSCKASGYIFTNYNMHWVQQTPG QGLEWIGAIYPRTGDTSYNQKFKGKATLTADKSSSTAYMQLS SLTSEDSAVYYCARDGFAYWGQG | Amino acid sequence of the heavy chain variable region ($V_H$) |
| 3 | IFTNYNMH | Amino acid sequence of the heavy chain CDRH 1 |
| 4 | AIYPRTGDTSYNQKFKG | Amino acid sequence of the heavy chain CDRH2 |
| 5 | ARDGFAY | Amino acid sequence of the heavy chain CDRH3 |
| 6 | GATATCCAGATGACACAGACTACATCCTCCCTGTCTGCCTCT CTGGGAGACAGAGTCACCATCAGTTGCAGGGCAAGTCAGGAC ATTAGCAATTATTTAAACTGGTATCAGCAGAAACCAGATGGA ACTGTTAAACTCCTGATCTACTACACATCAAGATTACACTCA GAAGTCCCATCAAGGTTCAGTGGCAGTGGGTCTGGAACAGAT TATTCTCTCACCATTAGCAACCTGGAGGAAGAAGATATTGCC ACTTACTTTTGCCAACAGGGTAAAACGCTTCCGTGGACGTTC GGTGGAGGC | Nucleic acid sequence of the light chain variable region ($V_L$) |
| 7 | DIQMTQTTSSLSASLGDRVTISCRASQDISNYLNWYQQKPDG TVKLLIYYTSRLHSEVPSRFSGSGSGTDYSLTISNLEEEDIA TYFCQQGKTLPWTFGGG | Amino acid sequence of the light chain variable region ($V_L$) |
| 8 | RASQDISNYLN | Amino acid sequence of the light chain CDRL 1 |
| 9 | YTSRLHS | Amino acid sequence of the light chain CDRL2 |
| 10 | QQGKTLPWT | Amino acid sequence of the light chain CDRL3 |

Example 2

Preparation of Mutated Antibodies Derived from cAb29

In order to map the residues in the cAb29 antibody that interact with *B. anthracis* protective antigen (PA) and are functionally required for binding of the antibody to PA, the antibody cAb29 was mutated as described below.

The wild type antibody PA29 as a single chain variable fragment (scFv) was randomly mutated using error-prone PCR under standard conditions. Mutated PCR-products were re-amplified, gel-purified, digested and ligated into a phage-display plasmid for the expression of a scFv-library displayed by m13 phage particles. Standard bio-panning technology was applied for the enrichment and screening of various mutated antibodies, resulting among other in the antibodies termed herein as PA29mut29, PA29mut33, PA29mut39, PA29mut40, and PA29mut41.

In order to examine the PA binding ability of the mutated antibodies, the mutated antibodies in the form of scFvs were screened using a direct ELISA assay. Briefly, phages were added to PA-coated plates and incubated for 2 hours. Plates were then washed, incubated with anti-M13-HRP detection antibody (GE healthcare) and developed using TMB (Pierce) as a substrate.

About 25% of the various mutated antibodies that were screened demonstrated improved binding as compared to the wild type scFv. The five mutated antibodies that demonstrated the highest binding signal (PA29mut29, PA29mut33, PA29mut39, PA29mut40, PA29mut41) were therefore sequenced.

The nucleic acid and amino acid sequences of the heavy and the light chains of the mutated antibodies PA29mut29, PA29mut33, PA29mut39, PA29mut40 and PA29mut41 are detailed in Table 2 below. The mutated amino acid residues are indicated by underlined bold letters.

In addition, the nucleic acid and amino acid sequences of the heavy and the light chains of the mutated antibody PA29mut29 and of the wild type chimeric antibody (termed PA29 w.t.) are shown in FIG. 1, and the nucleic acid and amino acid sequences of the heavy and the light chains of the mutated antibodies PA29mut33 and PA29mut39 and of the mutated antibodies PA29mut40 and PA29mut41 are shown in FIG. 2 and FIG. 3, respectively. The mutated nucleotides and amino acid residues are indicated by underlined bold letters.

TABLE 2

Sequences of mutated antibodies

| SEQ ID NO. | Sequence | Description |
|---|---|---|
| 11 | CAGGTTCAACTGCAGCAGTCTGGGGCTGAGCTGGTGA AGCCTGGGGCCTCAGTGAAGATGTCCTGCAAGGCTTC TGGCTACATATTTACCAATTACAATATGCACTGGGTAC AGCAGACACCTGGACAGGGCCTGGAATGGATTGGCGC CATTTATCCACGAACTGGTGATACTTCCTACAATCAGA AGTTCAAAGGCAAGGCCACATTGACCGCAGACAAATC CTCCAGCACAGCCTACATGCAGCTCAGCAGCCTGACA TCTGAGGATTCTGCGGTCTATTACTGTGCAAGAGACG GGTTTGCTTACTGGGGCCAAGGGACCACTCTCACAGT C | Nucleic acid sequence of the heavy chain variable region of PA29mut29 |
| 12 | QVQLQQSGAELVKPGASVKMSCKASGYIFTNYNMHWV QQTPGQGLEWIGAIYPRTGDTSYNQKFKGKATLTADKSS STAYMQLSSLTSEDSAVYYCARDGFAYWGQGTTLTV | Amino acid sequence of the heavy chain variable region of PA29mut29 |
| 13 | GATATCCAGATGACACAGACTACATCCTCCCTGTCTG CCTCTCTGGGAGACAGAGTCACCATCAGTTGCAGGGC AAGTCAGGACATTAGCAATTATTTAAACTGGTATCAG CAGAAACCAGATGGAACTGTTAAACTCCTGATCTACT ACACATCAAGATTACACTCAGGAGTCCCATCAAGGTT CAGTGGCAGTGGGTCTGGAACAGATTATTCTCTCACC ATTAGCAACCTGGAGGAAGAAGATATTGCCACTTACT ATTGCCAACAGGGTAAAACGCTTCCGTGGACGTTCGG TGGAGGCACCAAGCTGGAAATCAAA | Nucleic acid sequence of the light chain variable region of PA29mut29 |
| 14 | DIQMTQTTSSLSASLGDRVTISCRASQDISNYLNWYQQK PDGTVKLLIYYTSRLHSGVPSRFSGSGSGTDYSLTISNL EEEDIATYYCQQGKTLPWTFGGGTKLEIK | Amino acid sequence of the light chain variable region of PA29mut29 |
| 15 | GAGGTTCAACTGCAGCAGTCTGGGGCTGAGCTGGTGA AGCCTGGGGCCTCAGTGAAGATGTCCTGCAAGGCTTC TGGCTACATATTTACCAATTACAATATGCACTGGGTAC AGCAGACACCTGGACAGGGCCTGGAATGGATTGGCGC TATTTATCCACGAACTGGTGATACTTCCTACAATCAGA AGTTCAAAGGCAAGGCCACATTGACTGCAGACAAATC CTCCAGCACAGCCTACATGCAGCTCAGCAGCCTGACA | Nucleic acid sequence of the heavy chain variable region of |

TABLE 2-continued

Sequences of mutated antibodies

| SEQ ID NO. | Sequence | Description |
|---|---|---|
| | TCTGAGGATTCTGCGGTCTATTACTGTGCAAGAGACG GGTTTGCTTACTGGGGCCAAGGGACCACTCTCACAGT C | PA29mut33 |
| 16 | EVQLQQSGAELVKPGASVKMSCKASGYIFTNYNMHWV QQTPGQGLEWIGAIYPRTGDTSYNQKFKGKATLTADKSS STAYMQLSSLTSEDSAVYYCARDGFAYWGQGTTLTV | Amino acid sequence of the heavy chain variable region of PA29mut33 |
| 17 | GATATCCGGATGACACAGACTACATCCTCCCTGTCTG CCTCTCTGGGAGACAGAGTCACCATCAGTTGCAGGGC AAGTCAGGACATTAGCAATTATTTAAACTGGTATCAG CAGAAGCCAGATGGAACTGTTAAACTCCTGATCTACT ACACATCAAGATTACACTCAGAAGTCCCATCAAGGTT CAGTGGCAGTGGGTCTGGAACAGATTATTCTCTCACC ATTAGCAACCTGGAGGAAGAAGATATTGCCACTTACT TTTGCCAACAGGGTAAAACGCTTCCGTGGACGTTCGG TGGAGGCACCAAGCtGgAAATCAAA | Nucleic acid sequence of the light chain variable region of PA29mut33 |
| 18 | DIRMTQTTSSLSASLGDRVTISCRASQDISNYLNWYQQK PDGTVKLLIYYTSRLHSEVPSRFSGSGSGTDYSLTISNL EEEDIATYFCQQGKTLPWTFGGGTKLEIK | Amino acid sequence of the light chain variable region of PA29mut33 |
| 19 | CAGGTTCAACTGCAGCAGTCTGGGGCTGAGCTAGTGA AGCCTGGGGCCTCAGTGAAGATGTCCTGCAAGGCTTC TGGCTACATATTTACCAATTACAATATGCACTGGGTAC AGCAGACACCTGGACAGGGCCTGGAATGGATTGGCGC TATTTATCCACGAACTGGTGATACTTCCTACAATCAGA AGTTCAAAGGCAAGGCCACATTGACTGCAGACAAATC CTCCAGCACAGCCTACATGCAGCTCAGCAGCCTGACA TCTGAGGATTCTGCGGTCTATTACTGTGCAAGAGACG GGTTTGCTTACTGGGGCCAAGGGACCACTCTCACAGT C | Nucleic acid sequence of the heavy chain variable region of PA29mut39 |
| 20 | QVQLQQSGAELVKPGASVKMSCKASGYIFTNYNMHWV QQTPGQGLEWIGAIYPRTGDTSYNQKFKGKATLTADKSS STAYMQLSSLTSEDSAVYYCARDGFAYWGQGTTLTV | Amino acid sequence of the heavy chain variable region of PA29mut39 |
| 21 | GATATCCAGATGACACAGACTACATCCTCCCTGTCTG CCTCTCTGGGAGACAGAGTCACCGTCAGTTGCAGGGC AAGTCAGGACATTAGCAATTATTTAAACTGGTATCAG CAGAAACCAGATGGAACTGTTAAACTCCTGATCTACT ACACATCAAGATTACACTCAGAAGTCCCATCAAGGTT CAGTGGCAGTGGGTCTGGAACAGATTATTCTCTCACC ATTAGCAACCTGGAGGAAGAAGATATTGCCACTTACT TTTGCCAACAGGGTAAAACGCTTCCGTGGACGTTCGG TGGAGGCACCAAGCTGGAAATCAAA | Nucleic acid sequence of the light chain variable region of PA29mut39 |
| 22 | DIQMTQTTSSLSASLGDRVTVSCRASQDISNYLNWYQQK PDGTVKLLIYYTSRLHSEVPSRFSGSGSGTDYSLTISNL EEEDIATYFCQQGKTLPWTFGGGTKLEIK | Amino acid sequence of the light chain variable region of PA29mut39 |
| 23 | CAGGTTCAACTGCAGCAGTCTGGGGCTGAGCTGGTGA AGCCTGGGGCCTCAGTGAAGATGTCCTGCAAGGCTTC TGGCTACATATTTACCAATTACAATATGCACTGGGTAC AGCAGACACCTGGACAGGGCCTGGAATGGATTGGCGC TATTTATCCACGAACTGGTGATACTTCCTACAATCAGA AGTTCAAAGGCAAGGCCACATTGACTGCAGACAAATC | Nucleic acid sequence of the heavy chain variable |

TABLE 2-continued

Sequences of mutated antibodies

| SEQ ID NO. | Sequence | Description |
|---|---|---|
| | CTCCAGCACAGCCTACATGCAGCTCAGCAGCCTGACA TCTGAGGATTCTGCGGTCTATTACTGTGCAAGAGACG GGTTTGCTTACTGGGGCCAAGGGACCACTCTCACAGT C | region of PA29mut40 |
| 24 | QVQLQQSGAELVKPGASVKMSCKASGYIFTNYNMHWV QQTPGQGLEWIGAIYPRTGDTSYNQKFKGKATLTADKSS STAYMQLSSLTSEDSAVYYCARDGFAYWGQGTTLTV | Amino acid sequence of the heavy chain variable region of PA29mut40 |
| 25 | GATATCCAGATGACACAGACTACACCCTCCCTGTCTG CCTCTCTGGGGGACAGAGTCACCATCAGTTGCAGGGC AAGTCAGGACATTAGCAATTATTTAAACTGGTATCAG CAGAAACCAGATGGAACTGTTAAACTCCTGATCTACT ACACATCGAGATTACACTCAGAAGTCCCATCGAGGTT CAGTGGCAGTGGGTCTGGAACAGATTATTCTCTCACC ATTAGCAACCTGGAGGAAGAAGATATTGCCACTTACT TTTGCCAACAGGGTAAAACGCTTCCGTGGACGTTCGG TGGAGGCACCAAGCTGGAAATCAAA | Nucleic acid sequence of the light chain variable region of PA29mut40 |
| 26 | DIQMTQTTPSLSASLGDRVTISCRASQDISNYLNWYQQK PDGTVKLLIYYTSRLHSEVPSRFSGSGSGTDYSLTISNL EEEDIATYFCQQGKTLPWTFGGGTKLEIK | Amino acid sequence of the light chain variable region of PA29mut40 |
| 27 | CAGGTTCAACTGCAGCAGTCTGGGGCTGAGCTGGTGA AGCCTGGGGTCTCAGTGAAGATGTCCTGCAAGGCTTC TGGCTACATATTTACCAATTACAATATGCACTGGGTAC AGCAGACACCTGGACAGGGCCTGGAATGGATTGGCGC TATTTATCCACGAACTGGTGATACTTCCTACAATCAGA AGTTCAAAGGCAAGGCCACATTGACTGCAGACAAATC CTCCAGCACAGCCTACATGCAGCTCAGCAGCCTGACA TCTGAGGATTCTGCGGTCTATTACTGTGCAAGAGACG GGTTTGCTTACTGGGGCCAAGGGACCACTCTCACAGT C | Nucleic acid sequence of the heavy chain variable region of PA29mut41 |
| 28 | QVQLQQSGAELVKPGVSVKMSCKASGYIFTNYNMHWV QQTPGQGLEWIGAIYPRTGDTSYNQKFKGKATLTADKSS STAYMQLSSLTSEDSAVYYCARDGFAYWGQGTTLTV | Amino acid sequence of the heavy chain variable region ($V_H$) of PA29mut41 |
| 29 | GATATCCAGATGACACAGACTACATCCTCCCTGTCTG CCTCTCTGGGAGACAGAGTCACCATCAGTTGCAGGGC AAGTCAGGACATTAGCAATTATTTAAACTGGTATCAG CAGAAACCAGATGGAACTGTTAAACTCCTGATCTACT ACACATCAAGATTACACTCAGAAGTCCCATCAAGGTT CAGTGGCAGTGGGTCTGGAACAGATTATTCTCTCACC ATTAGCAACCTGGAGGAAGAAGATATTGCCACTTACT TTTGCCAACAGGGTAAAACGCTTCCGTGGACGTTCGG TGGAGGCACCAAGCTGGAAATCAAA | Nucleic acid sequence of the light chain variable region of PA29mut41 |
| 30 | DIQMTQTTSSLSASLGDRVTISCRASQDISNYLNWYQQK PDGTVKLLIYYTSRLHSEVPSRFSGSGSGTDYSLTISNL EEEDIATYFCQQGKTLPWTFGGGTKLEIK | Amino acid sequence of the light chain variable region ($V_L$) of PA29mut41 |

Alignments of the heavy chain variable domains of the wild type and mutated antibodies are shown in FIG. 4A, FIG. 4B and FIG. 4C for the heavy chain variable domain CDRH1, CDRH2 and CDRH3, respectively. The CDRs are shown in grey boxes and the mutated amino acid residues are indicated by bold underlined letters.

Alignments of the light chain variable domains of the wild type and mutated antibodies are shown in FIG. 5A, FIG. 5B and FIG. 5C for the light chain variable domain CDRL1, CDRL2 and CDRL3, respectively. The CDRs are shown in grey boxes and the mutated amino acid residues are indicated by bold underlined letters.

The invention claimed is:

1. An isolated monoclonal antibody or any antigen-binding fragment thereof which binds to *Bacillus anthracis* protective antigen, wherein the antibody comprises a heavy chain variable region comprising:
   a) the complementarity determining region CDRH1 comprising the amino acid sequence of IFTNYNMH denoted by SEQ ID NO. 3;
   b) the complementarity determining region CDRH2 comprising the amino acid sequence AIYPRTGDTSYNQKFKG denoted by SEQ ID NO. 4; and
   c) the complementarity determining region CDRH3 comprising the amino acid sequence ARDGFAY denoted by SEQ ID NO. 5; and
   a light chain variable region comprising:
   d) the complementarity determining region CDRL1 comprising the amino acid sequence RASQDISNYLN denoted by SEQ ID NO. 8;
   e) the complementarity determining region CDRL2 comprising the amino acid sequence YTSRLHS denoted by SEQ ID NO. 9; and
   f) the complementarity determining region CDRL3 comprising the amino acid sequence QQGKTLPWT denoted by SEQ ID NO. 10.

2. The isolated monoclonal antibody according to claim 1, wherein said heavy chain variable region is encoded by a nucleic acid sequence which is at least 70% identical to SEQ ID NO. 1 and wherein said light chain variable region is encoded by a nucleic acid sequence which is at least 70% identical to SEQ ID NO. 6.

3. The isolated monoclonal antibody according to claim 1, wherein said heavy chain variable region is of the amino acid sequence denoted by SEQ ID NO. 2 or a variant thereof in which at least one position selected from the group consisting of position 1 and position 16 of SEQ ID NO. 2 is substituted.

4. The isolated monoclonal antibody according to claim 1, wherein said light chain variable region is of the amino acid sequence denoted by SEQ ID NO. 7 or a variant thereof in which at least one position selected from the group consisting of positions 3, 9, 21, 57 and 87 of SEQ ID NO. 7 is substituted.

5. The isolated monoclonal antibody according to claim 1, wherein said heavy chain variable region is of the amino acid sequence denoted by SEQ ID NO. 2 and wherein said light chain variable region is of the amino acid sequence denoted by SEQ ID NO. 7.

6. The isolated monoclonal antibody according to claim 1, wherein said antibody is a chimeric, a humanized or a human antibody.

7. The isolated monoclonal antibody according to claim 1, wherein said antibody is an antibody fragment selected from the group consisting of Fv, single chain Fv (scFv), heavy chain variable region, light chain variable region, Fab, F(ab)$_2$' and any combination thereof.

8. A pharmaceutical composition comprising as an active ingredient the isolated monoclonal antibody or any antigen-binding fragment thereof of claim 1 and a pharmaceutically acceptable carrier, excipient or diluent.

9. The pharmaceutical composition according to claim 8, wherein said composition further comprises at least one additional anti-anthrax agent.

10. A kit comprising:
    (i) an isolated monoclonal antibody or any antigen-binding fragment thereof which binds to *Bacillus anthracis* protective antigen, wherein the antibody comprises a heavy chain variable region comprising:
        a) the complementarity determining region CDRH1 comprising the amino acid sequence of IFTNYNMH denoted by SEQ ID NO. 3;
        b) the complementarity determining region CDRH2 comprising the amino acid sequence AIYPRTGDTSYNQKFKG denoted by SEQ ID NO. 4; and
        c) the complementarity determining region CDRH3 comprising the amino acid sequence ARDGFAY denoted by SEQ ID NO. 5; and
    a light chain variable region comprising:
        d) the complementarity determining region CDRL1 comprising the amino acid sequence RASQDISNYLN denoted by SEQ ID NO. 8;
        e) the complementarity determining region CDRL2 comprising the amino acid sequence YTSRLHS denoted by SEQ ID NO. 9; and
        f) the complementarity determining region CDRL3 comprising the amino acid sequence QQGKTLPWT denoted by SEQ ID NO. 10; and
    (ii) instructions for use.

11. An isolated chimeric antibody, or any antigen-binding fragment thereof which binds to *Bacillus anthracis* protective antigen, wherein the antibody comprises a heavy chain variable region comprising:
    a) the complementarity determining region CDRH1 comprising the amino acid sequence of IFTNYNMH denoted by SEQ ID NO. 3;
    b) the complementarity determining region CDRH2 comprising the amino acid sequence AIYPRTGDTSYNQKFKG denoted by SEQ ID NO. 4; and
    c) the complementarity determining region CDRH3 comprising the amino acid sequence ARDGFAY denoted by SEQ ID NO. 5; and
    a light chain variable region comprising:
    d) the complementarity determining region CDRL1 comprising the amino acid sequence RASQDISNYLN denoted by SEQ ID NO. 8;
    e) the complementarity determining region CDRL2 comprising the amino acid sequence YTSRLHS denoted by SEQ ID NO. 9; and
    f) the complementarity determining region CDRL3 comprising the amino acid sequence QQGKTLPWT denoted by SEQ ID NO. 10.

12. The isolated chimeric antibody according to claim 11, wherein the antibody comprises a heavy chain variable region of the amino acid sequence denoted by SEQ ID NO. 2, or a variant thereof in which at least one position selected from the group consisting of position 1 and position 16 of SEQ ID NO. 2 is substituted, and a light chain variable region of the amino acid sequence denoted by SEQ ID NO. 7, or a variant thereof in which at least one position selected from the group consisting of positions 3, 9, 21, 57 and 87 of SEQ ID NO. 7 is substituted.

* * * * *